(12) United States Patent
Jinno et al.

(10) Patent No.: US 8,237,388 B2
(45) Date of Patent: Aug. 7, 2012

(54) MANIPULATOR AND CONTROL METHOD THEREFOR

(75) Inventors: Makoto Jinno, Ota-ku (JP); Takamitsu Sunaoshi, Yokohama (JP); Shigeru Omori, Ashigarakami-gun (JP)

(73) Assignees: Terumo Kabushiki Kaisha, Tokyo (JP); Kabushiki Kaisha Toshiba, Tokyo (JP)

( * ) Notice: Subject to any disclaimer, the term of this patent is extended or adjusted under 35 U.S.C. 154(b) by 1131 days.

(21) Appl. No.: 12/061,092

(22) Filed: Apr. 2, 2008

(65) Prior Publication Data

US 2008/0245175 A1    Oct. 9, 2008

(30) Foreign Application Priority Data

Apr. 3, 2007    (JP) ................ 2007-097752

(51) Int. Cl.
G05B 11/01    (2006.01)
(52) U.S. Cl. ......... 318/560; 318/690; 318/691; 74/469; 74/479.01; 74/490.01; 606/1; 606/130
(58) Field of Classification Search ............ 318/560, 318/690, 691; 74/490.01, 479.01, 469; 606/1, 606/130
See application file for complete search history.

(56) References Cited

U.S. PATENT DOCUMENTS

| | | | |
|---|---|---|---|
| 3,952,880 A * | 4/1976 | Hill et al. ............... | 414/5 |
| 6,027,238 A * | 2/2000 | Nagashima ............. | 700/69 |
| 6,865,446 B2 * | 3/2005 | Yokono et al. ......... | 700/245 |
| 6,889,116 B2 | 5/2005 | Jinno | |
| 6,899,705 B2 * | 5/2005 | Niemeyer ............... | 606/1 |
| 7,300,373 B2 | 11/2007 | Jinno et al. | |
| 2005/0179416 A1 * | 8/2005 | Iribe et al. ............. | 318/563 |
| 2005/0200324 A1 * | 9/2005 | Guthart et al. ......... | 318/568.11 |
| 2006/0219065 A1 * | 10/2006 | Jinno et al. ............ | 81/383 |
| 2007/0151389 A1 * | 7/2007 | Prisco et al. ........... | 74/490.05 |
| 2007/0200525 A1 * | 8/2007 | Kanaoka ................. | 318/568.21 |

FOREIGN PATENT DOCUMENTS

| | | |
|---|---|---|
| JP | 10-329063 | 12/1998 |
| JP | 2002-102248 | 4/2002 |
| JP | 2004-301275 | 10/2004 |
| JP | 2006-305717 | 11/2006 |

OTHER PUBLICATIONS

Office Action issued Aug. 30, 2011 in Japanese Patent Application No. 2007-097752 (English translation of pertinent portion).
Office Action issued Mar. 6, 2012, in Japanese Patent Application No. 2007-097752 with partial English translation.

* cited by examiner

*Primary Examiner* — Walter Benson
*Assistant Examiner* — Kawing Chan
(74) *Attorney, Agent, or Firm* — Oblon, Spivak, McClelland, Maier & Neustadt, L.L.P.

(57) ABSTRACT

A manipulator has a working unit including an end effector and a posture axis for changing the orientation of the manipulator, a compound mechanism provided on the working unit, and a controller for actuating a gripper axis, a yaw axis, and a roll axis by respectively controlling movement positions of three motors. The controller includes a torque generation detector for detecting a timing at which torque is generated on the gripper axis. When the controller detects the timing at which a torque $\tau_{g'}$ is generated on the gripper axis under operation of a given motor, the movement positions of the plural motors are shifted and set, corresponding to the directions at which interference torques are generated with respect to the yaw axis and the roll axis, and to predetermined positions of the same directions.

18 Claims, 28 Drawing Sheets

FIG. 28

| CONTENTS | AXIS | YR MECHANISM (10a) | DIFFERENTIAL MECHANISM (10b) | SAME SIDE GEAR ARRANGEMENT (10c) |
|---|---|---|---|---|
| REQUIRED TORQUE DURING GRIPPING | $\tau_1$ | 2 | 1(1/2) | 0(0) |
| | $\tau_2$ | -1 | 0(0) | 1(1) |
| | $\tau_3$ | 1 | 1(1) | 1(1) |
| WIRE ELONGATION DURING GRIPPING | $\theta_1$ | 2 | 1(1/2) | 0(0) |
| | $\theta_2$ | -1 | 0(0) | 1(1) |
| | $\theta_3$ | 1 | 1(1) | 1(1) |
| AMOUNT OF POSTURE CHANGE UPON GRIPPING | $\theta_y$ | 2 | 0.5(1/4) | 0(0) |
| | $\theta_r$ | 3 | 0.5(1/6) | 1(1/3) |
| | $\theta_{g'}$ | 6 | 2(1/3) | 2(1/3) |

MANIPULATOR AND CONTROL METHOD THEREFOR

BACKGROUND OF THE INVENTION

1. Field of the Invention

The present invention relates to a manipulator having an operating section including an end effector axis and one or more posture axes by which the orientation of the end effector axis is changed, together with a control method therefor. In particular, the present invention relates to a manipulator equipped with a compound mechanism for operating the end effector axis and the posture axes thereof, and to a control method for such a manipulator.

2. Description of the Related Art

In laparoscopic surgery, a number of small holes are opened in a patient's abdomen or the like, and an endoscope, a manipulator (or forceps), or the like is inserted, and surgery is carried out while the surgeon observes an image from the endoscope on a monitor. In this type of laparoscopic surgery, owing to the fact that opening of the abdominal cavity is unnecessary, the burden on the patient is small, and number of days required for the post-operative recovery and number of days spent in the hospital can be significantly reduced. Therefore, laparoscopic surgical operations are expected to find an increased range of applications.

On the other hand, manipulators used in laparoscopic surgery are desirably capable of quick and appropriate surgical techniques depending on the position and size of the affected region, and are used to perform various surgical techniques like suture, ligature, knot-tying and removing of the affected part of the patient. For this purpose, the present applicant has developed and proposed manipulators which have a high degree of freedom for manipulation and which can easily be operated (see, for example, Japanese Laid-Open Patent Publication No. 2002-102248 and Japanese Laid-Open Patent Publication No. 2004-301275).

With manipulators used for performing laparoscopic surgery, so as to enable various techniques to be performed, it is desirable for the posture of the end or tip of the end effector to possess a high degree of freedom. In this context, the provision of a compound mechanism for operating the end effector axis and the posture axes by which the orientation of the end effector axis is changed may be conceived of.

For example, in the event that the manipulator comprises the end effector axis and yaw and roll axes, wherein the respective axes are operated via wires, due to the fact that there is a mechanical relative influence therebetween, for operating either one of these axes, a compound mechanism is operated by operating two or more wires in a coordinated fashion.

Incidentally, as recognized by the present inventor, with this type of compound mechanism, when a torque is generated with respect to one axis, mechanically, an interference torque is generated on the other axes and on the actuator, such that unnecessary and wasted motion occurs at the other axis. In particular, in the case that the tip of the end effector grips a needle or a living body organism (hereinafter referred to also as a workpiece), or when shearing or the like is carried out, comparatively large torques are required, such that the collaterally generated interference torque becomes large, and unnecessary movement generated at the other axes easily arises. It is thought that such movements may also lead to cases where some sense of uneasiness is felt by the operator.

In order to prevent the generation of unnecessary movement by such interference torques, it is necessary to provide thick wires so as to obtain sufficient rigidity. However, when thick wires are used, it is required to make the longitudinal connecting portion through which the wire is inserted between the manipulator and the working unit large in diameter, and corresponding thereto, a need arises to set the holes, which are provided in the patient's abdomen or the like, to be quite large in size.

SUMMARY OF THE INVENTION

It is one object of the present invention to provide a manipulator and control method therefor, in which a high level of freedom can be attained, yet wherein even if torque is applied with respect to one axis, the device can be controlled such that unnecessary movements do not occur at the other axes.

According to an aspect of the present invention, there is provided a manipulator comprising a working unit including an end effector axis and at least one posture axis by which an orientation of the end effector axis is changed, a compound mechanism disposed on the working unit for operating the end effector axis and the posture axis, an end effector axis actuator for driving the end effector axis, and at least one posture axis actuator for driving the posture axis, a controller for controlling movement positions of the end effector axis actuator and the posture axis actuator, thereby operating the end effector axis and the posture axis, and a torque generation detector for detecting a timing at which torque is generated on at least one of the end effector and the posture axis. When the torque generation detector detects the timing, the controller controls the movement position of the posture axis actuator so as to be shifted by a predetermined amount in a same direction as a direction at which an interference torque is generated by the compound mechanism.

According to another aspect of the present invention, there is provided a manipulator comprising a working unit including an end effector axis and a first posture axis and a second posture axis by which an orientation of the end effector axis is changed, a compound mechanism disposed on the working unit for operating the end effector axis, the first posture axis, and the second posture axis, and an end effector axis actuator for driving the end effector axis, and a first posture axis actuator and a second posture axis actuator for driving the first posture axis and the second posture axis separately or in a combined manner. A torque for driving the end effector axis generates an interference torque on the first posture axis actuator at the first posture axis of the compound mechanism, and the torque and the interference torque act in opposite directions at the second posture axis of the compound mechanism.

The above and other objects features and advantages of the present invention will become more apparent from the following description when taken in conjunction with the accompanying drawings, in which preferred embodiments of the present invention are shown by way of illustrative example.

BRIEF DESCRIPTION OF THE DRAWINGS

FIG. 28 is a chart illustrating applied torques, wire elongations, and posture change amounts, in respective configurations of the manipulators.

DESCRIPTION OF THE PREFERRED EMBODIMENTS

Descriptions of first, second and third embodiments of a working mechanism and a manipulator according to the present invention shall be presented below with reference to the accompanying FIGS. 1 through 28. The manipulator 10a (see FIG. 1) according to the first embodiment, the manipulator 10b (see FIG. 15) according to the second embodiment, and the manipulator 10c (see FIG. 23) according to the third embodiment are utilized for performing medical procedures such as laparoscopic surgery and the like.

The manipulator 10a is used for performing prescribed treatments by gripping a part of a living body or a curved needle or the like at the end of a working unit 12a, which typically is referred to as a grasping forceps or a needle driver (needle holder).

Figure 1:
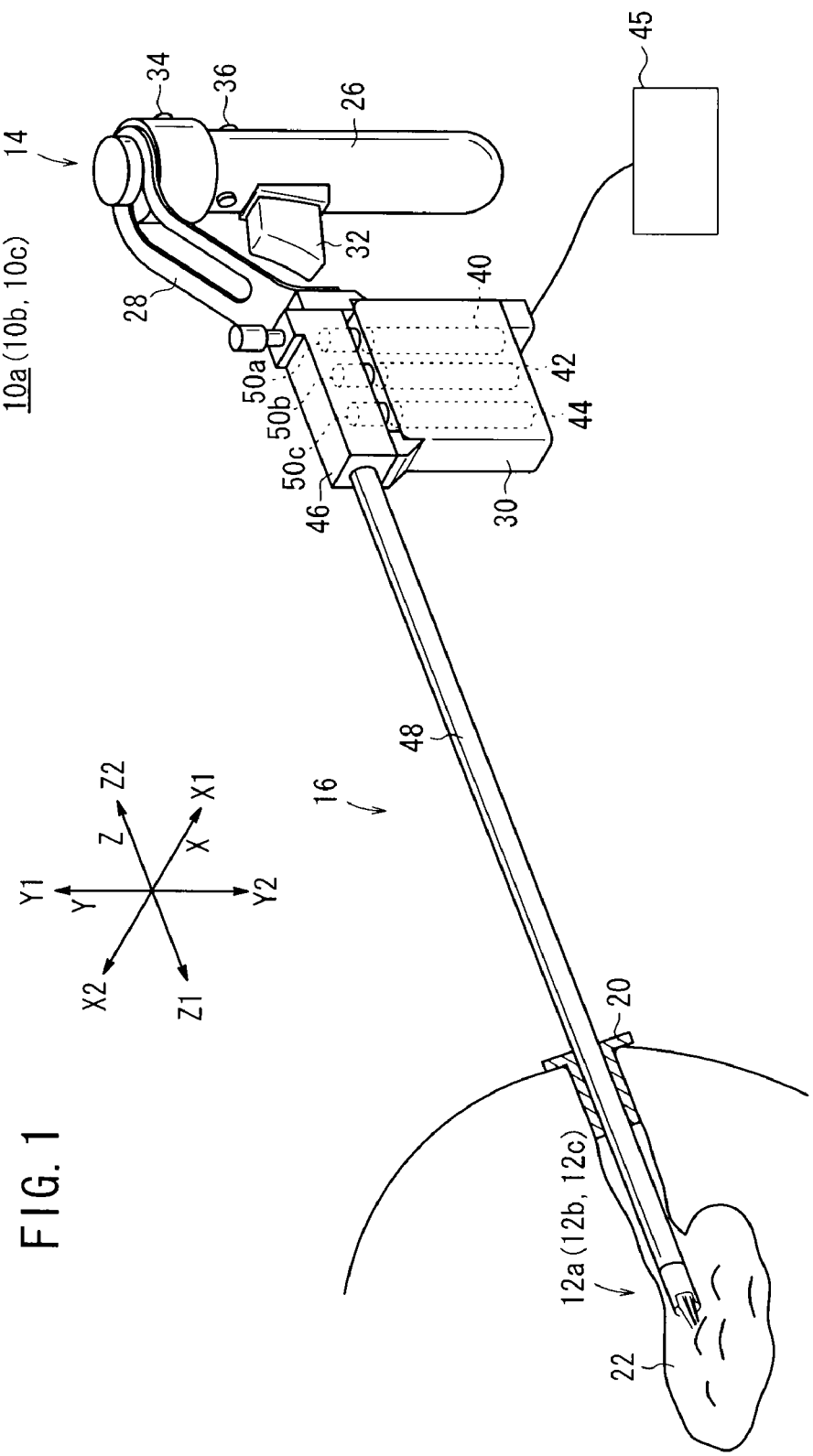
FIG. 1 is a perspective view of a manipulator according to a first embodiment.

As shown in FIG. 1, the manipulator 10a includes an operation command unit 14 on a proximal end thereof which is held or operated by the hand, the working unit 12a on the distal end thereof for working on a living tissue, and an elongate connector 16 interconnecting the working unit 12a and the operation command unit 14. The working unit 12a and the connector 16 are of a narrow diameter and can be inserted into a body cavity 22 through a trocar 20 in the form of a hollow cylinder mounted in an abdominal region or the like of the patient. The working unit 12a is actuated by the operation command unit 14 to perform various techniques to remove, grip, suture, or tie-knot an affected part of the patient's body in the body cavity 22.

Figure 15:
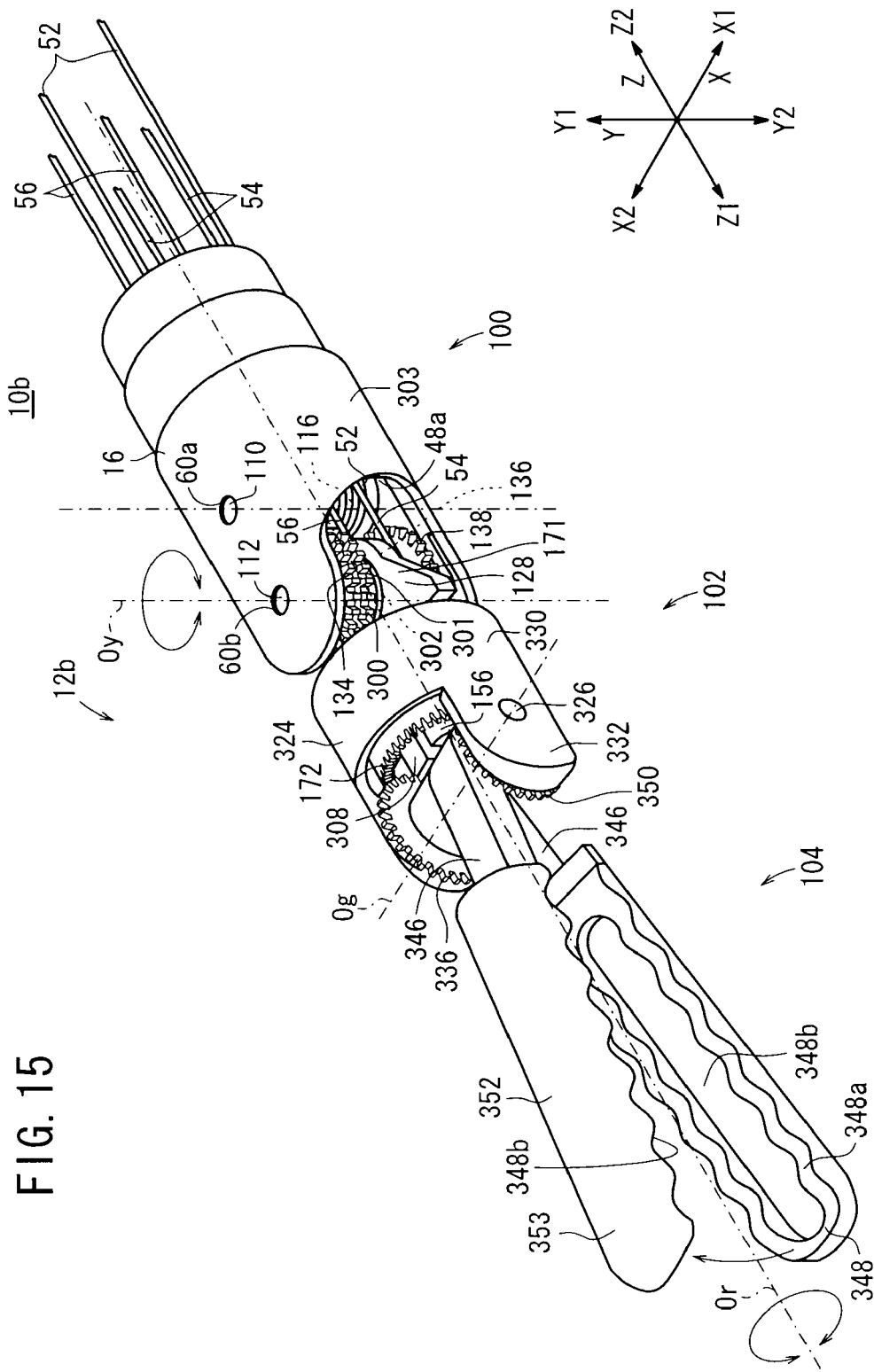
FIG. 15 is a perspective view of a working unit in the manipulator according to the second embodiment.
Figure 16:
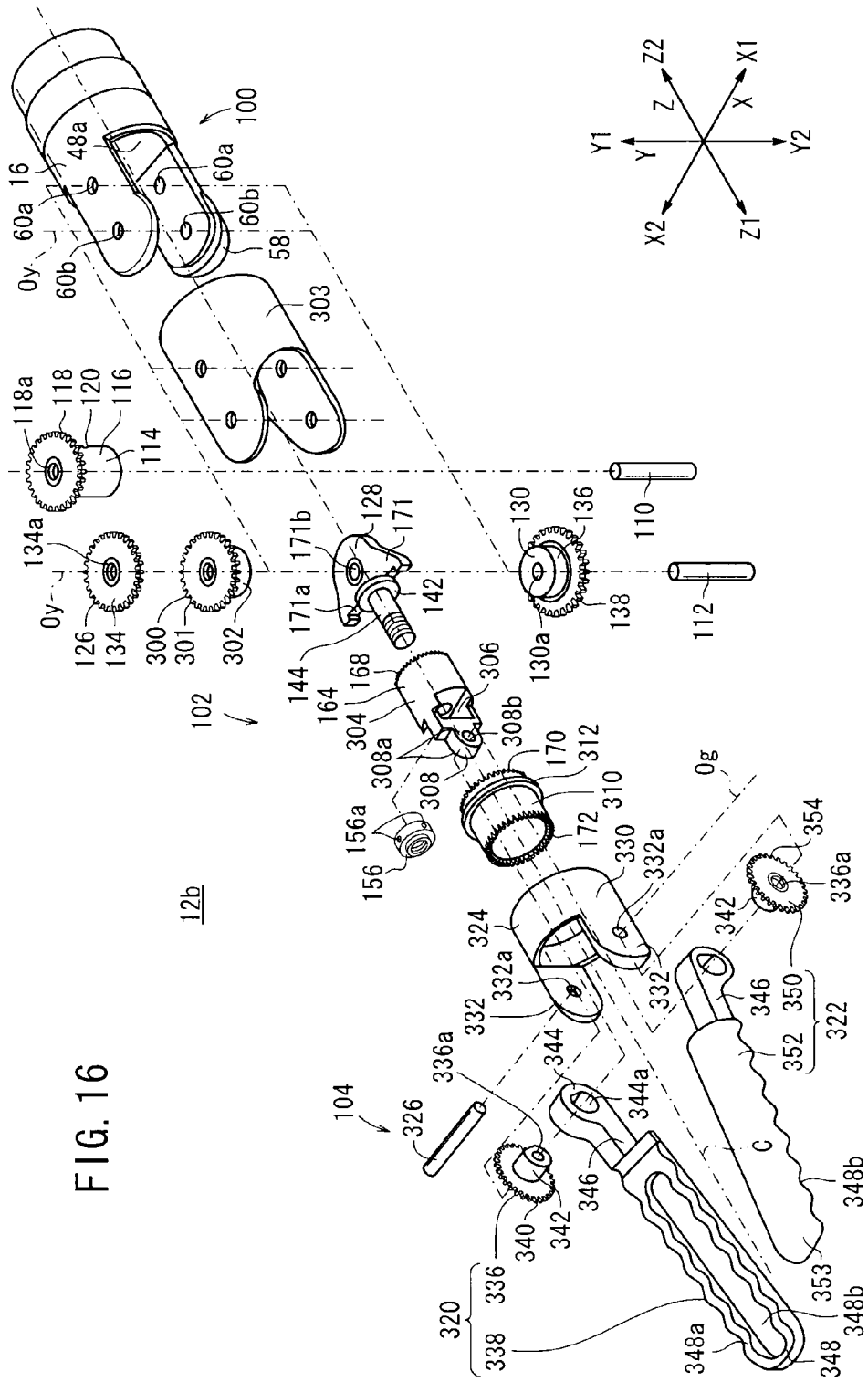
FIG. 16 is an exploded perspective view of the working unit in the manipulator according to the second embodiment.
Figure 17:
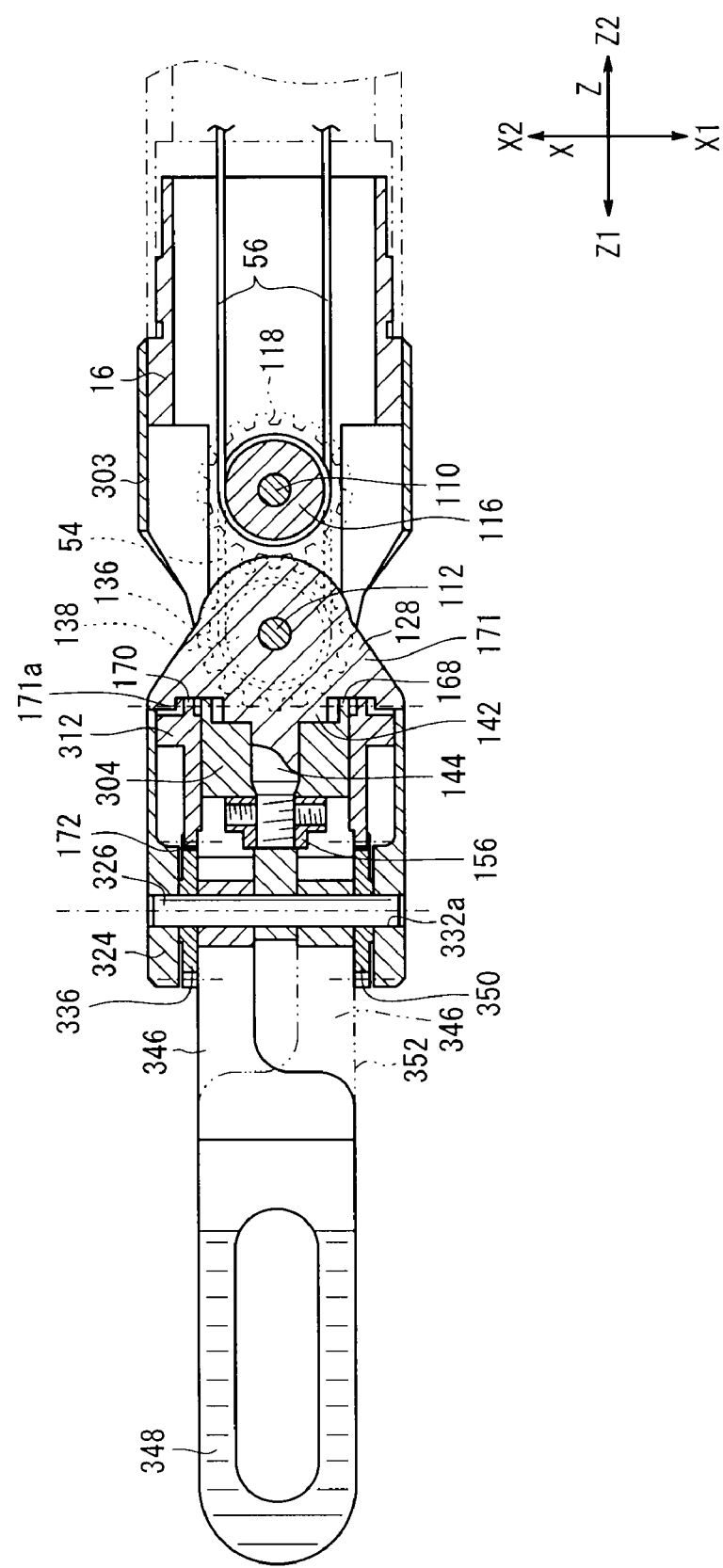
FIG. 17 is a cross sectional plan view of a working unit in the manipulator according to the second embodiment.
Figure 23:
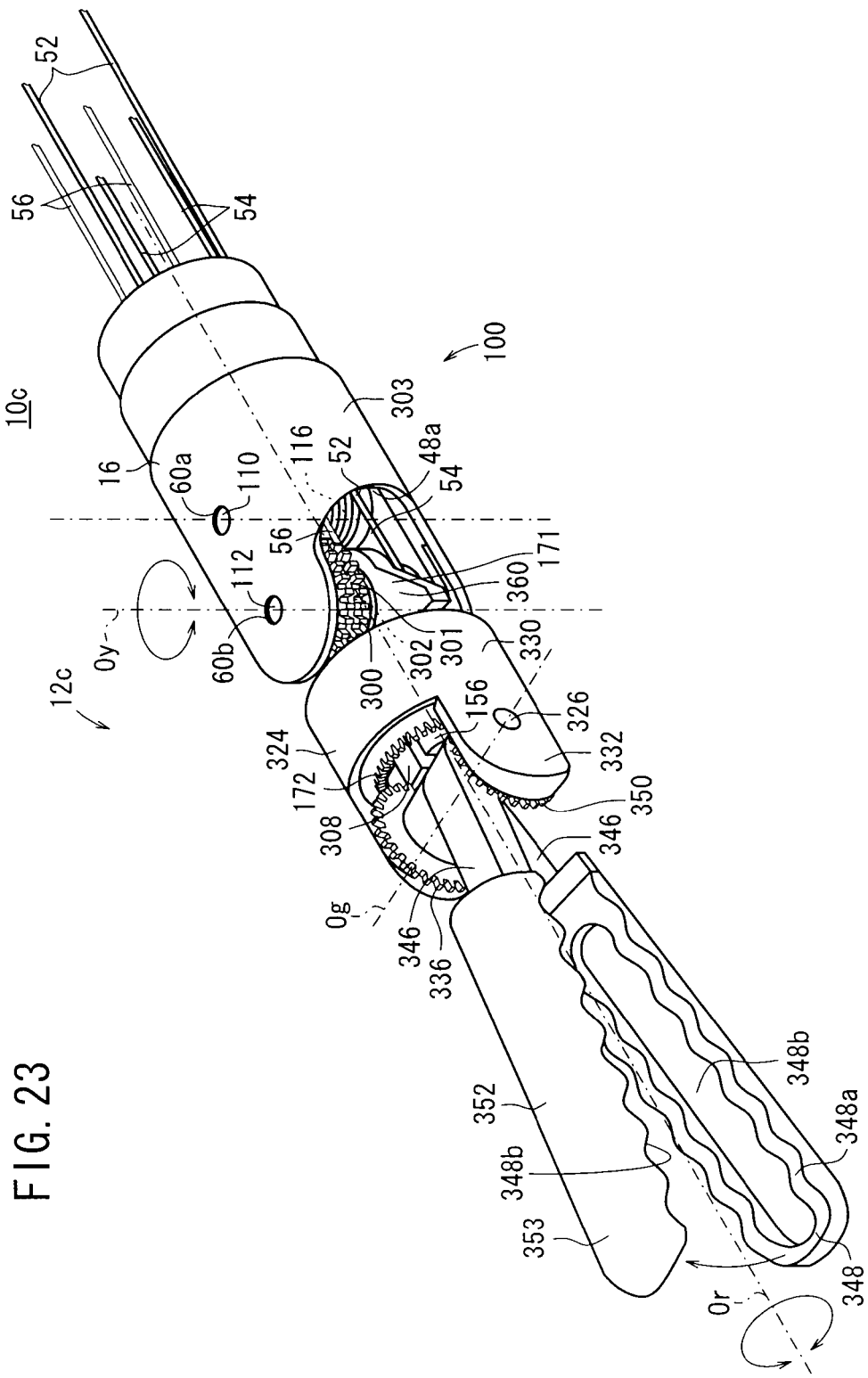
FIG. 23 is a perspective view of a working unit in a manipulator according to a third embodiment.
Figure 24:
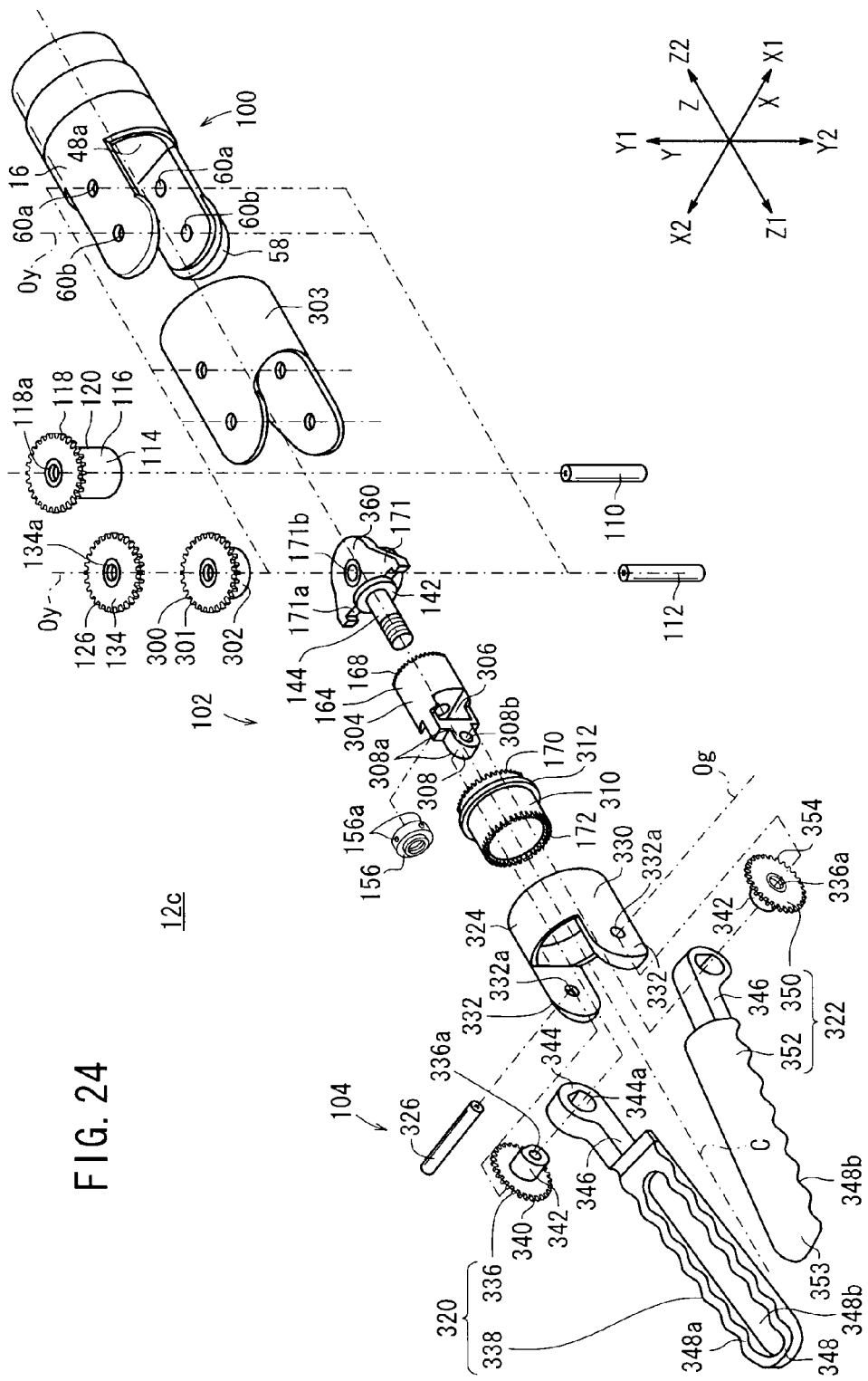
FIG. 24 is an exploded perspective view of the working unit in the manipulator according to the third embodiment.
Figure 25:
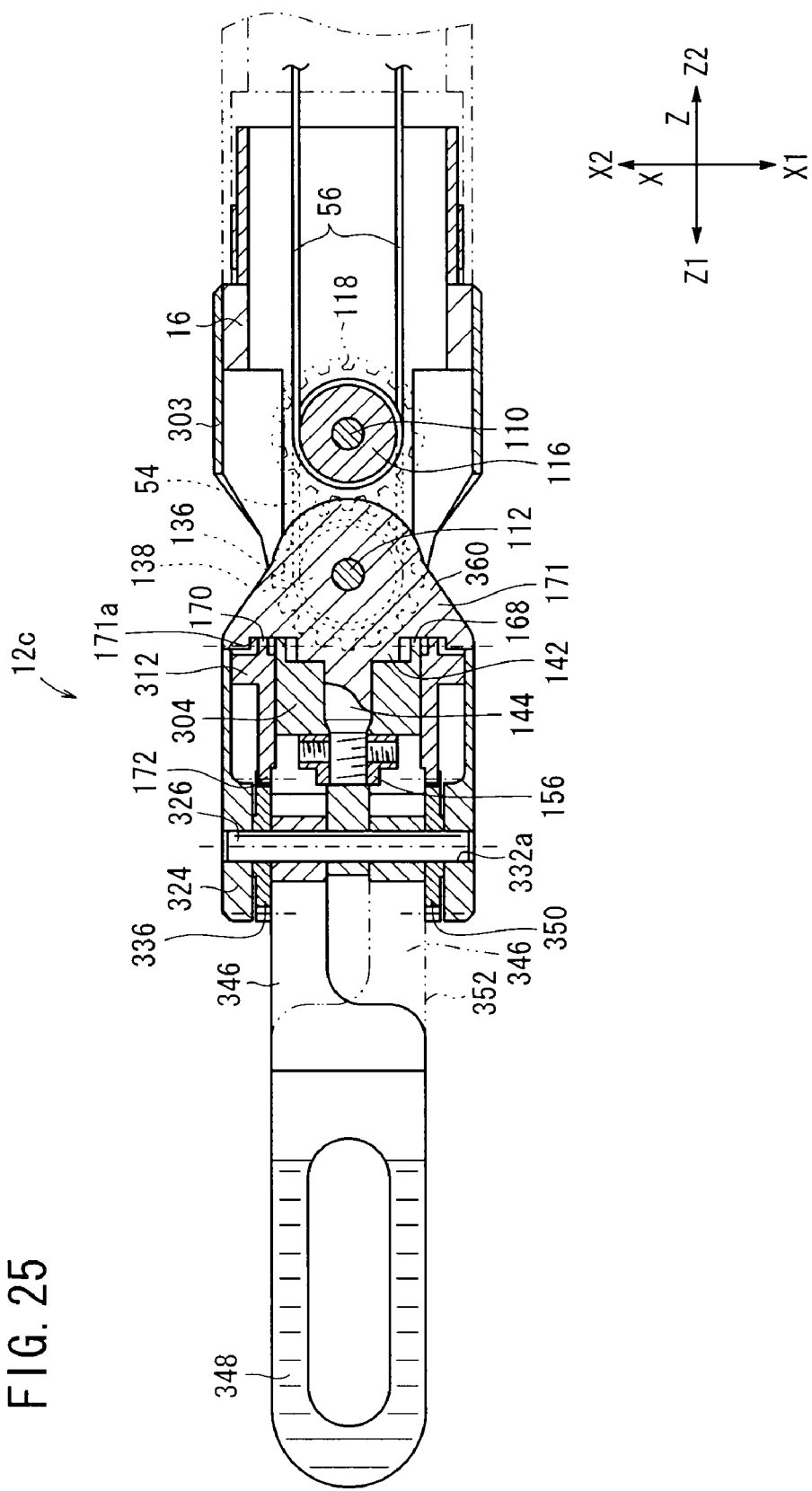
FIG. 25 is a cross sectional plan view of the working unit in the manipulator according to the third embodiment.
Figure 26:
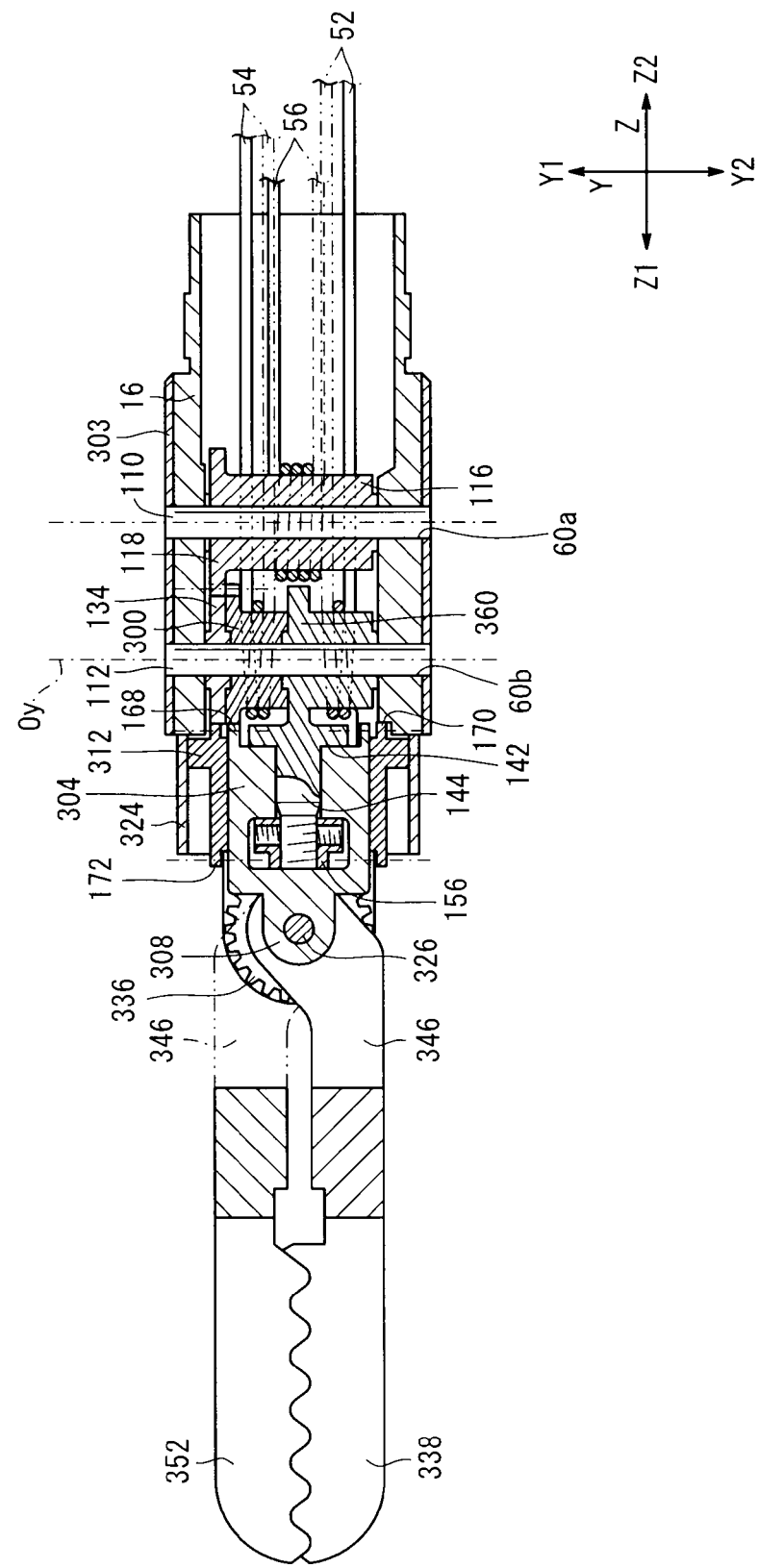
FIG. 26 is a cross sectional side view of the working unit in the manipulator according to the third embodiment.

In FIGS. 1, 15 and 23, it is assumed in the following descriptions that the transverse direction is referred to as an X direction, the vertical direction thereof as a Y direction, and the longitudinal directions of the connector 16 as a Z direction. Further, among the X directions, the rightward direction is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Moreover, unless otherwise noted, these directions represent directions of the manipulators 10a, 10b, and 10c when they are in a neutral posture (i.e., the postures shown in FIGS. 2, 15 and 23). The definitions of the above directions are for illustrative purposes only, and the manipulators 10a, 10b and 10c can be used in any of various orientations (e.g., the manipulators may be used upside down).

The operation command unit 14 includes a grip handle 26 gripped by hand, an arm 28 extending from an upper portion of the grip handle 26, and an actuator block 30 connected to a distal end of the arm 28. The grip handle 26 includes a trigger lever 32, a first instruction lever 34, and a second instruction lever 36, which are operable by the finger. The trigger lever 32 is disposed in a position where it can easily be pulled by the index finger.

The actuator block 30 houses therein three motors 40, 42, 44 corresponding to respective mechanisms of three degrees of freedom, which are incorporated in the working unit 12a. The motors 40, 42, 44 are arrayed parallel to each other in the longitudinal direction of the connector 16. The motors 40, 42, 44 are small in size and diameter, thereby making the actuator block 30 compact and flat in shape. The actuator block 30 is disposed downwardly of the end of the operation command unit 14, in the Z1 direction. In addition, the motors 40, 42, 44 rotate under the control of a controller 45 based on the operation of the operation command unit 14.

The connector 16 includes a joint 46 joined to the actuator block 30 and a hollow connecting shaft 48 extending in the Z1 direction from the joint 46. The joint 46 houses therein a drive pulley 50a, a drive pulley 50b, and a drive pulley 50c, which are rotatable and are connected respectively to the drive axes of the motors 40, 42, 44. A wire 52, a wire 54, and a wire 56, serving as flexible members, are trained respectively around the drive pulleys 50a, 50b, 50c, and extend through a space 48a (see FIG. 2) in the connecting shaft 48 to the working unit 12a. The flexible members are motive force transmitting members, drive members or drive systems, which are deformed by elasticity or backlash. The wires 52, 54, 56 may be of the same type and same diameter. The wires 52, 54, 56 will collectively be referred to as wires 57.

The joint 46 can be operated according to a predetermined process to disconnect the connector 16 from the operation command unit 14 for cleaning, sterilization, maintenance, and the like. Further, the end portion from the connector 16 is replaceable. For example, depending on the technique required for a certain surgical operation, the connector 16 may be replaced with a connector having a different length and/or the working unit 12a may be replaced with a working unit incorporating different mechanisms.

Figure 2:
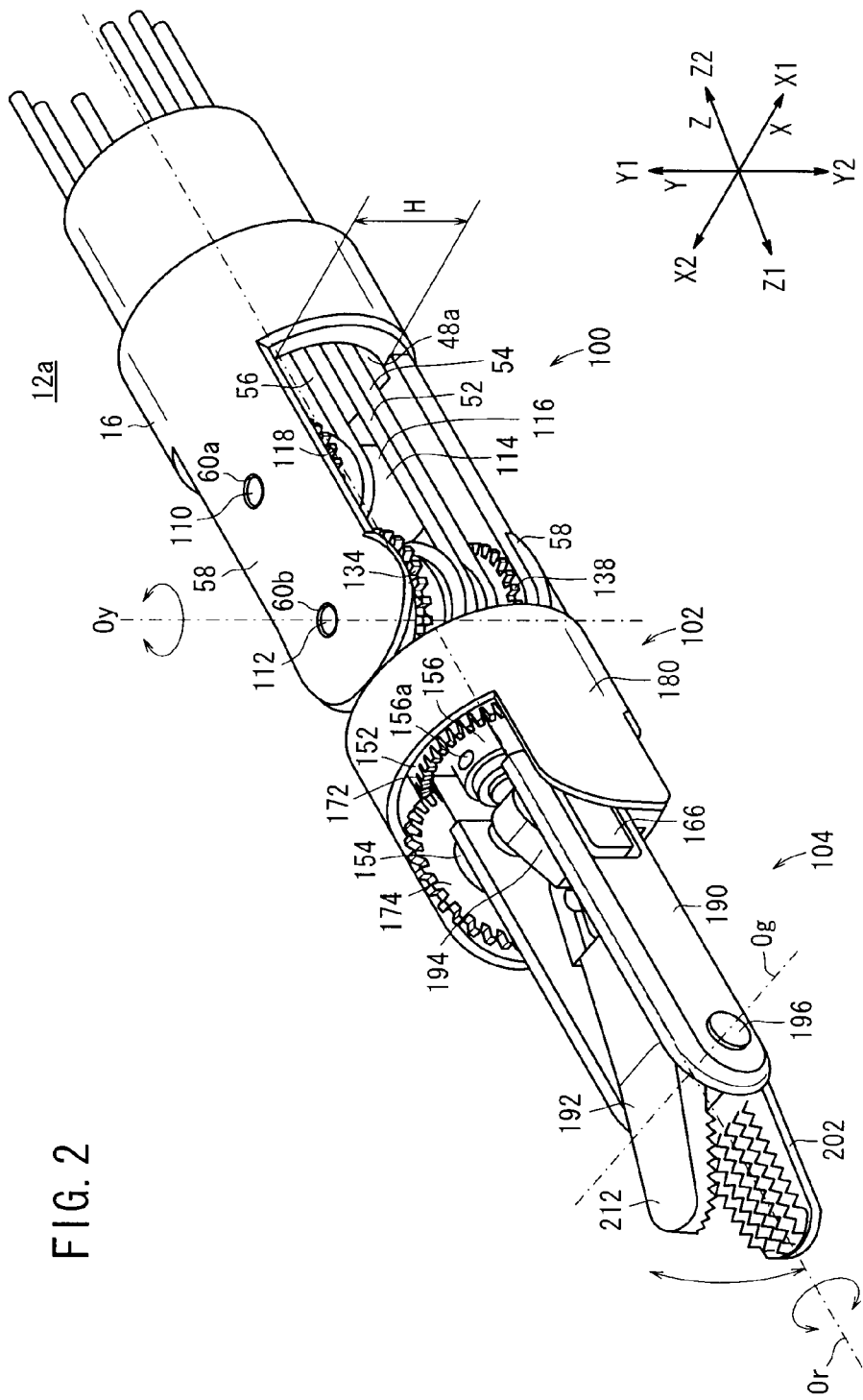
FIG. 2 is a perspective view of a working unit in the manipulator according to the first embodiment.

As shown in FIG. 2, the connector 16 has a pair of diametrically opposite tongues 58 projecting toward the distal end thereof and arranged in facing relation to the central axis of the connecting shaft 48. The space 48a in the connecting shaft 48 communicates with a space between the tongues 58. The tongues 58 have two axially spaced pairs of axis holes 60a, 60a and 60b, 60b defined respectively therein, which are positioned in confronting relation with each other. The tongues 58 have respective arc shaped distal ends. The two tongues 58 have respective flat inner surfaces that face each other, which are formed in parallel with each other, and are spaced from each other by a distance H.

The two axis holes 60a, 60a and the two axis holes 60b, 60b are disposed one on each side so as to sandwich the central axis of the connector 16 therebetween. The axis holes 60a, 60b are juxtaposed along the Z direction, and the axis holes 60b are arranged closer to the distal end side than the axis holes 60a.

As shown in FIG. 2, the working unit 12a incorporates therein mechanisms having three degrees of freedom. These mechanisms include a mechanism having a first degree of freedom for angularly moving a portion of the working unit 12a that is positioned ahead of a first rotational axis Oy extending along the Y directions, in yawing directions about the first rotational axis (second posture axis) Oy, a mechanism having a second degree of freedom for angularly moving the portion of the working unit 12a in rolling directions about a second rotational axis (first posture axis) Or extending along the Z direction, and a mechanism having a third degree of freedom for opening and closing an end effector 104 on the distal end of the working unit 12a about a third rotational axis (end effector axis) Og.

The end effector 104 is a component that actually performs work during an operation. The first rotational axis Oy and the second rotational axis Or are provided so as to enable the posture (attitude) of the end effector 104 to be changed, so that work can be easily performed. Hereinbelow, the mechanism having the third degree of freedom for opening and closing the end effector 104 shall be referred to as a gripper axis, the mechanism with the first degree of freedom that rotates in yawing directions shall be referred to as the yaw axis, and the mechanism with the second degree of freedom that rotates in rolling directions shall be referred to as the roll axis.

The working unit 12a comprises a wire-driven mechanism 100, a compound mechanism (mechanical unit) 102, and the end effector 104.

Figure 3:
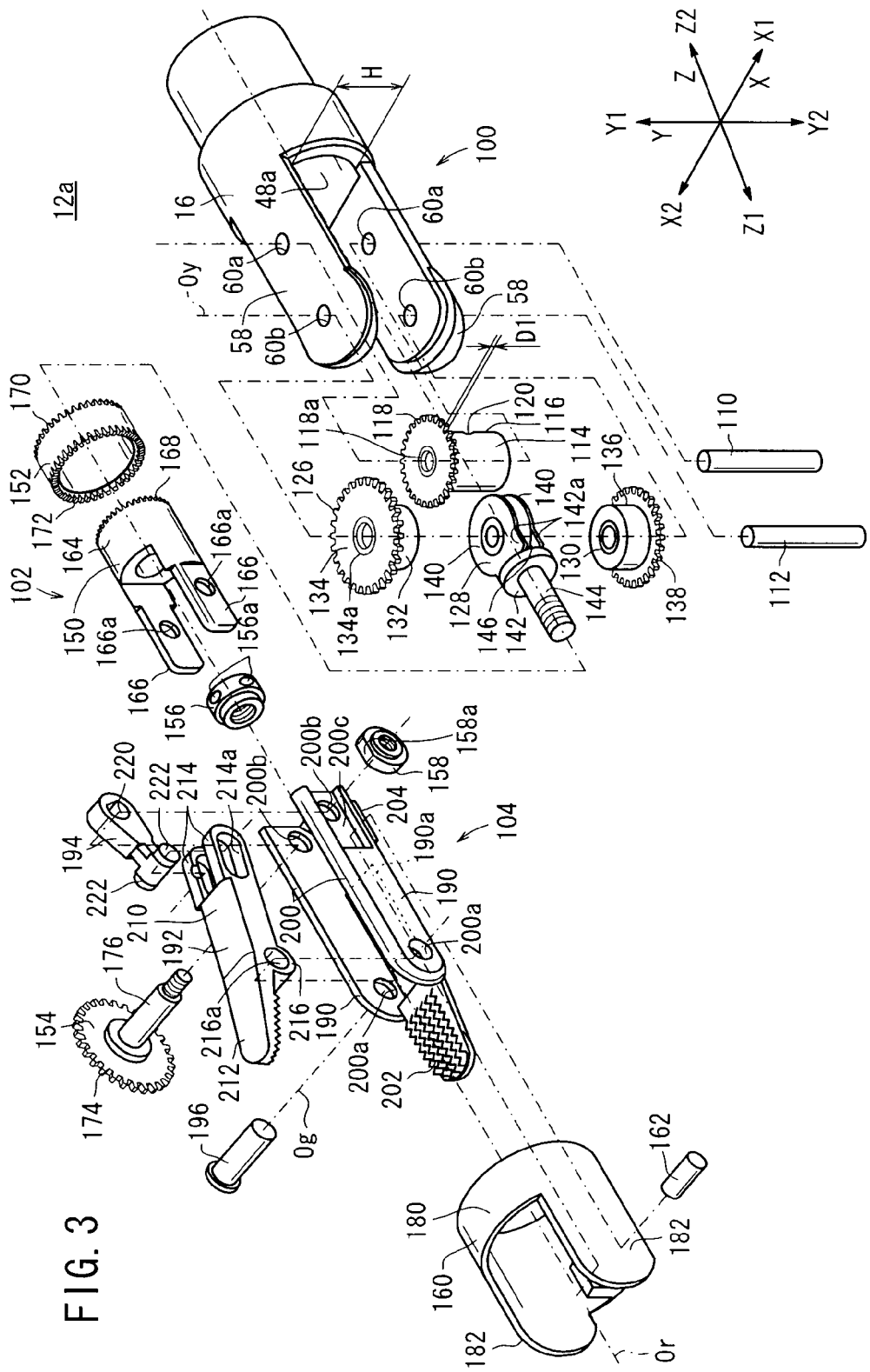
FIG. 3 is an exploded perspective view of the working unit in the manipulator according to the first embodiment.
Figure 4:
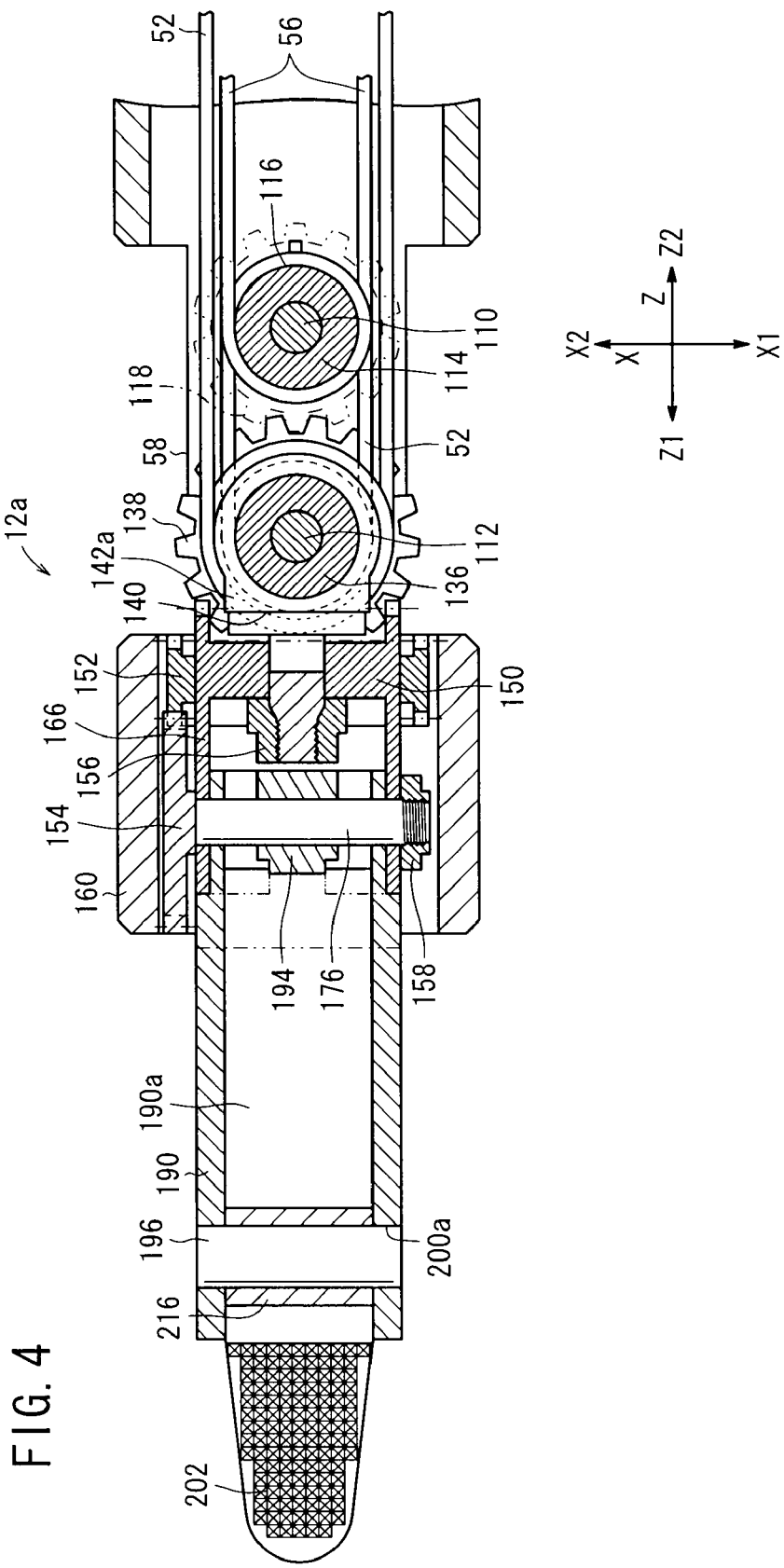
FIG. 4 is a cross sectional plan view of the working unit in the manipulator according to the first embodiment.
Figure 5:
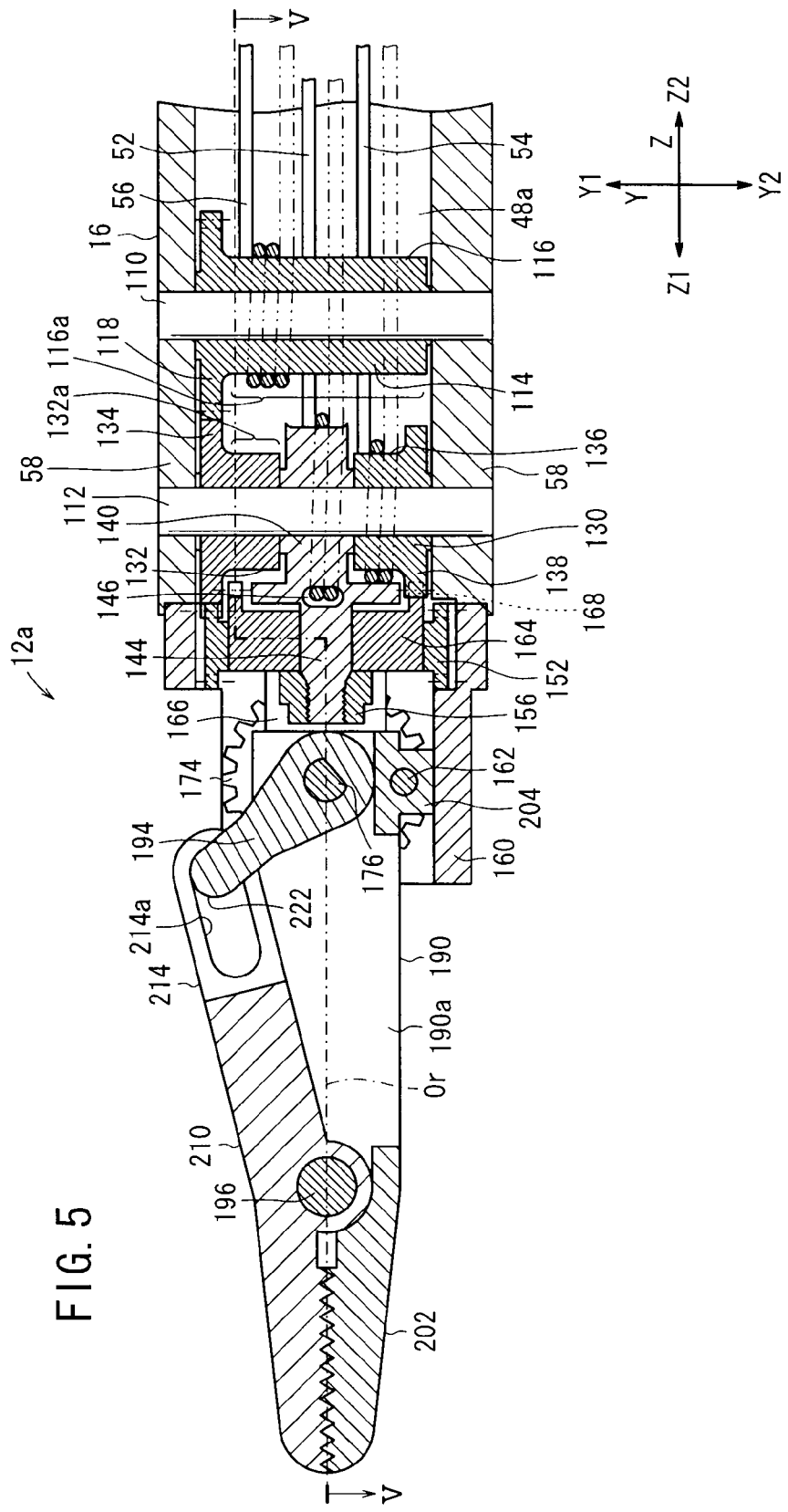
FIG. 5 is a cross sectional side view of the working unit in the manipulator according to the first embodiment.

The wire-driven mechanism 100, the compound mechanism 102, and the end effector 104 shall be described in detail with reference to FIGS. 2 through 4.

The wire-driven mechanism 100 is disposed between the pair of tongues 58 and serves to convert circulative movements of the respective wires 52, 54, 56 into rotational movements and transmit the rotational movements to the compound mechanism 102. The wire-driven mechanism 100 includes a shaft 110 inserted in the axis holes 60a, 60a, a shaft 112 inserted in the axis holes 60b, 60b, and a gear body 114 rotatably supported on the shaft 110. The shafts 110 and 112 are press-fitted and fixed securely into the axis holes 60a, 60b. The shaft 112 is axially aligned with the first rotational axis Oy.

The gear body 114 comprises a tubular member 116 and a gear 118 disposed concentrically on an upper portion of the tubular member 116. The gear 118 comprises a spur gear greater in diameter than the tubular member 116. Unless otherwise specified, a gear referred to herein comprises a spur gear. The gear body 114 has a height, which is substantially equal to the distance H, and is rotatably disposed between the pair of tongues 58. The gear 118 has a thickness D1 sufficiently smaller than the height H, so that the height (H−D1) of the tubular member 116 takes up a substantial portion of the height H between the tongues 58. The gear 118 has a low annular rib 118a disposed on the upper surface thereof around the hole through which the shaft 110 is inserted. The annular rib 118a prevents the upper surface of the gear 118 from contacting the upper tongue 58, thereby reducing sliding resistance therebetween.

Figure 6:
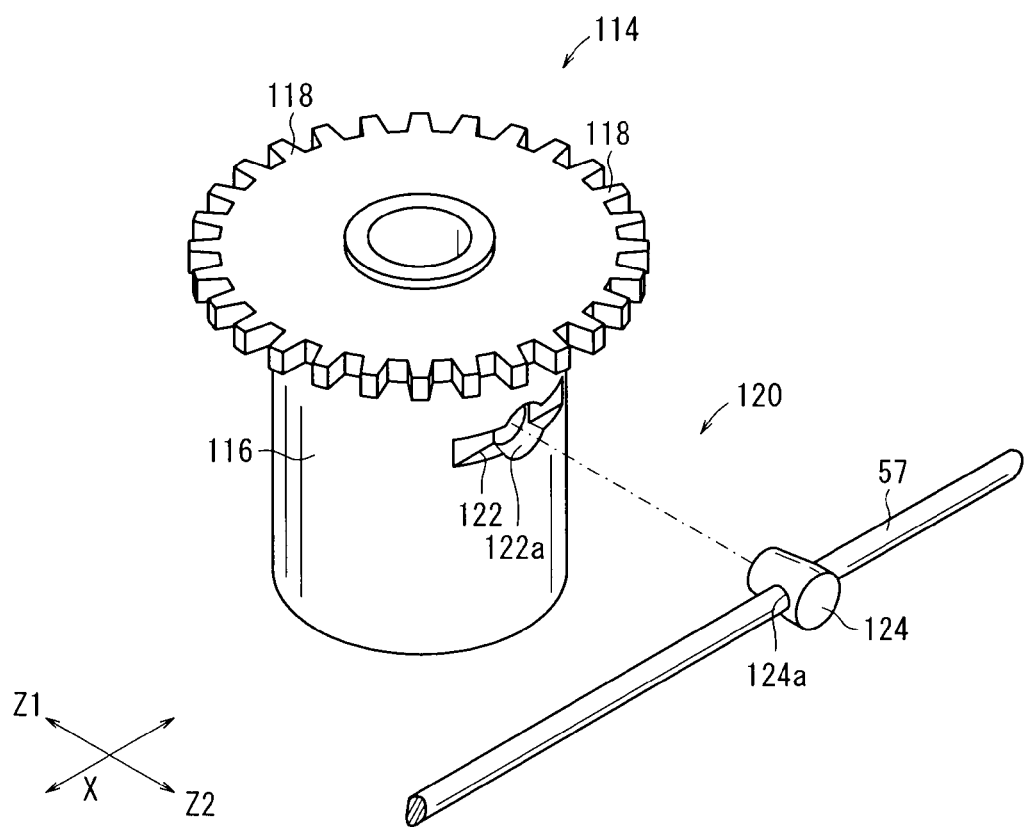
FIG. 6 is an exploded perspective view of a wire fixing mechanism.

As shown in FIG. 6, the tubular member 116 is combined with a wire securing mechanism 120. The wire securing mechanism 120 has a groove 122 defined in an upper portion of the side of the tubular member 116 which faces in the Z2 direction and extends laterally in the X direction when the gear body 114 is in a neutral position, and a tapered fastening pin 124 disposed centrally in the groove 122. The groove 122 has a recess 122a positioned at the center thereof, into which the fastening pin 124 is inserted and fixed. The groove 122 may be slightly inclined in alignment with a turn of the wire 57, which is helically wound around the tubular member 116.

The groove 122 has a width and a maximum depth that are essentially equal to the diameter of the wire 57. The fastening pin 124 has a hole 124a defined laterally therethrough, through which the wire 57 is capable of penetrating. The wire 57 is threaded through the hole 124a, and the fastening pin 124 is inserted into the recess 122a, thereby fitting the wire 57 partially within the groove 122. The wire 57 is thus oriented horizontally and fastened to the tubular member 116.

Returning to FIGS. 2 through 4, the compound mechanism 102 is a mechanism that serves both to open and close the end effector 104, as well as to, in combination therewith, cause a change in the posture of the end effector 104.

The compound mechanism 102 comprises a gear body 126, a main axis member 128, and a gear body 130, which are rotatably supported on the shaft 112, and are arranged successively from the Y1 direction toward the Y2 direction.

The gear body 126 comprises a tubular member 132 and a gear (perpendicular axis rotor) 134 disposed concentrically on an upper portion of the tubular member 132. The gear 134 has the same thickness as the gear 118 and is held in mesh with the gear 118. The gear 134 has a greater number of gear teeth than the gear 118 and can transmit the rotation of the gear 118 at a reduced speed (while increasing torque). Naturally, depending on design conditions, rotation may also be transmitted at the same speed or at a higher speed. The gear 134 has a low annular rib 134a disposed on the upper surface thereof around the hole through which the shaft 112 is inserted. The annular rib 134a prevents the upper surface of the gear 134 from contacting the upper tongue 58, thereby reducing the sliding resistance therebetween.

The gear body 130 is essentially identical in shape to the gear body 126, but is in an upside-down orientation with respect to the gear body 126. The gear body 130 comprises a tubular member 136 and a gear 138 disposed concentrically on a lower portion of the tubular member 136. The tubular member 136 is substantially identical in diameter and shape to the tubular member 132. The gear 138 has a number of teeth, which may be slightly smaller than the teeth of the gear 134. The tubular member 136 is combined with a wire securing mechanism 120, which is similar to the wire securing mechanism 120 of the tubular member 116, disposed on a side surface of the tubular member 136 that faces the Z2 direction, such that the wire 54 is fastened to the tubular member 136 by the wire securing mechanism 120.

The main axis member 128 has a tubular member 140 through which the shaft 112 is inserted, an annular seat 142 facing the Z1 direction, and a support bar 144 extending from the center of the annular seat 142 in the Z1 direction. The support bar 144 is aligned axially with the second rotational axis Or. The support bar 144 has an externally threaded distal end portion.

The annular seat 142 is slightly spaced from an outer side surface of the tubular member 140, with two short upper and lower bridges 142a interposed therebetween. A vertical hole 146, which is slightly elongated in the Y direction, is defined between the annular seat 142 and the tubular member 140, so as to be capable of receiving the wire 52 that is inserted therethrough. The tubular member 140 is combined with a wire securing mechanism 120, which is similar to that of the tubular member 116, on the side surface of the tubular member 140 that faces the Z2 direction, such that the wire 52 is fastened to the tubular member 140 by the wire securing mechanism 120.

Along with circulatory movement of the wire 52, the main axis member 128 rotates in yawing directions about the first rotational axis Oy, so that the support bar 144 can swing in an XZ plane.

The tubular member 140, the gear body 126, and the gear body 130 are stacked together along the shaft 112, forming an axis thereof, and have a combined height which is essentially equal to the height H, such that they are disposed with substantially no gaps between the pair of tongues 58.

The compound mechanism 102 further comprises a drive base 150, a gear ring 152, a geared pin 154, fastening nuts 156, 158, and a cover 160. The fastening nut 156 has a plurality of radial fine holes 156a defined therein for insertion of a narrow rotary tool. At least one of the fine holes 156a is exposed radially (see FIG. 2), for enabling the fastening nut 156 to be turned without the need for removal of the cover 160. The fastening nut 158 has parallel surfaces 158a, which are engageable by a rotary tool such as a wrench or the like.

The drive base 150 includes a tubular member 164 rotatably fitted over a proximal end portion of the support bar 144, a pair of support arms 166 projecting in the Z1 direction from both left and right ends of the tubular member 164, and a face gear 168 disposed on a surface of the tubular member 164 that faces the Z2 direction. Each of the support arms 166 serves to support the end effector 104, and has respective holes 166a defined therein, which are aligned in the X direction. After the tubular member 164 has been inserted into the proximal end portion of the support bar 144, the fastening nut 156 is threaded over the externally threaded distal end portion of the support bar 144, whereby the drive base 150 is rotatably supported on the support bar 144 for rotation in rolling directions centrally about the support bar 144 (i.e., about the second rotational axis Or).

The face gear 168 is held in mesh with the gear 138. Consequently, the drive base 150 is rotatable about the second rotational axis Or, in response to rotation of the tubular member 136.

The gear ring 152 is in the form of a thin tubular member including a face gear 170 on a surface thereof facing the Z2 direction, and a face gear 172 on a surface thereof facing the Z1 direction. The gear ring 152 is fitted over the tubular member 164 of the drive base 150 for sliding rotation with respect to the outer circumferential surface of the tubular member 164. The gear ring 152 is fitted over the tubular member 164 such that the face gear 170 is slightly displaced off the face gear 168 of the drive base 150 in the Z1 direction, until being held in mesh with the gear 134. The face gear 170 meshes with the gear 134, such that the gear ring 152 is rotatable about the second rotational axis Or accompanying rotation of the gear body 126.

The gear-attached pin 154 includes a gear 174, which meshes with the face gear 172, and a pin 176 extending in the X1 direction from the center of the gear 174. The pin 176 has an externally threaded distal end portion. The pin 176 passes through the two holes 166a such that the threaded distal end portion projects from one of the support arms 166, and the fastening nut 158 is threaded thereover. Owing thereto, the gear-attached pin 154, with the gear 174 meshing with the face gear 172, is rotatably supported by the support arms 166. Further, the pin 176 is cut in a D-shaped cross section, for engagement with a portion of the end effector 104.

The cover 160 serves to protect the components of the compound mechanism 102, covering the gear ring 152 and the gear 174 such that they are not exposed radially. The cover 160 includes a short tube 180 extending in the Z2 direction, and a pair of ears 182 that project in the Z1 direction, from respective left and right end portions of the short tube 180. The ears 182 are shaped such that circumferential wall portions of the short tube 180 extend in the Z1 direction while maintaining the same diameter. The cover 160 has a lower portion fastened to a portion of the end effector 104 by a cover-fastening pin 162. The cover 160 has a diameter, which is equal to or smaller than the connector 16 when viewed in front elevation.

With such a compound mechanism 102, when the gear body 130 rotates, the rotation thereof is transmitted from the gear 138 to the face gear 168, such that the drive base 150 and the end effector 104 connected thereto can be rotated about the second rotational axis Or. Further, when the gear body 114 rotates, the rotation thereof is transmitted from the gear 118 to the pin 176 through the gear 134, the face gear 170, the face gear 172, and the gear 174, such that the geared pin 154 can be rotated.

The cover 160 may be in the form of a hollow cylindrical or conical cover for covering the compound mechanism 102 and the end effector 104, almost in their entirety, to such an extent that operation of the compound mechanism 102 and the end effector 104 will not be hampered. The cover 160 may also be fastened using a pin 196.

The end effector 104 comprises a first end effector member 190, a second end effector member 192, a link 194, and the pin 196. The pin 196 is axially aligned with the third rotational axis Og.

The first end effector member 190 includes a pair of laterally spaced side walls 200 facing each other and having respective holes 200a defined in front end portions of the side walls 200 and respective holes 200b defined in rear end portions of the side walls 200, a first gripper 202 (end effector axis) projecting in the Z1 direction from lower front end portions of the side walls 200, and a cover mount 204 disposed on rear lower end portions of the side walls 200. The holes 200a have diameters such that the pin 196 can be press-fitted therein. The first gripper 202 narrows in width slightly along the Z1 direction and is formed with an arcuate distal end portion. The first gripper 202 has a number of small closely spaced conical upper projections disposed over the entire surface thereof substantially without gaps and facing in the Y1 direction.

The front end portions of each of the side walls 200 are arcuate in shape, whereas both outer side surfaces of the rear end portions thereof have respective recesses 200c defined therein in which the support arms 166 are fitted. A hole 190a (see FIG. 4) is defined between the first gripper 202 and the cover mount 204 for preventing interference with respect to the rear end portion of the second end effector member 192. The cover mount 204 has a hole defined therein into which the cover-fastening pin 162 is press-fitted.

The second end effector member 192 comprises a base 210, a second gripper (end effector axis) 212 extending from the front end of the base 210 in the Z1 direction, a pair of ears 214 extending in the Z2 direction from both left and right rear end portions of the base 210, and a shaft support sleeve 216 disposed on a lower surface of the front end of the base 210. The shaft support sleeve 216 has a hole 216a defined therein which has an inside diameter large enough to enable the pin 196 to be inserted therein. When the pin 196 is inserted into the shaft support sleeve 216 and press-fitted in the hole 200a, the second end effector member 192 is made swingable centrally about the third rotational axis Og. The second gripper 212 is identical in shape to the first gripper 202, but is arranged in an upside-down orientation with respect to the first gripper 202. When the second end effector member 192 is rotated about the third rotational axis Og, the second gripper 212 is brought into abutment against the first gripper 202, so that a curved needle or the like can be gripped therebetween. The ears 214 have oblong holes 214a defined respectively therein.

The link 194 has a hole 220 defined in an end thereof and a pair of engaging fingers 222 disposed on the other end, which project laterally away from each other. The engaging fingers 222 slidably engage in the respective oblong holes 214a. The hole 220 is cut in a D-shaped cross section for receiving the pin 176 snugly therein, and thus, the hole 220 serves to position the pin 176 and prevent the pin 176 from rotating about its own axis. When the pin 176 is inserted in the holes 166a, as well as in the holes 200b, 220, the fastening nut 158 is threaded over the distal end portion of the pin 176, and the link 194 is made swingable about the pin 176.

The wire 52 is wound for 1.5 turns around the tubular member 140, the wire 54 is wound 1.5 turns around the tubular member 136, and the wire 56 is wound 2.5 turns (900°) around the tubular member 116. As made clear from FIG. 4, the diameter of the tubular member 140 is set to a value equal to or greater than the sum of the diameter of the tubular member 116 and the diameters of the two wires 56. As viewed in plan, the wires 52, 54 are disposed slightly outwardly of the wire 56. Therefore, each of the wires is easily prevented from interfering with each other.

Specifically, since the wire 56 is disposed inwardly of the wire 52, wire 56 does not interfere with the wire 52. Accordingly, without concern to the position of the wire 52, the wire 56 can be wound around the tubular member 116 over a region 116a thereof, which is about two-thirds of the overall height (H−D1) of the tubular member 116. The region 116a is wide enough to allow the wire 56 to be wound 2.5 turns (or even more, e.g., 3.5 turns (1260°)) therearound, so that the gear body 114 can be rotated to make 2.5 revolutions (or more). Further, since the rotation amount of the gear body 114 is large, the gear ratio between the gear 118 and the gear 134 can be set largely, thereby enabling an increase in the rotational torque of the gear body 126.

Figure 7:
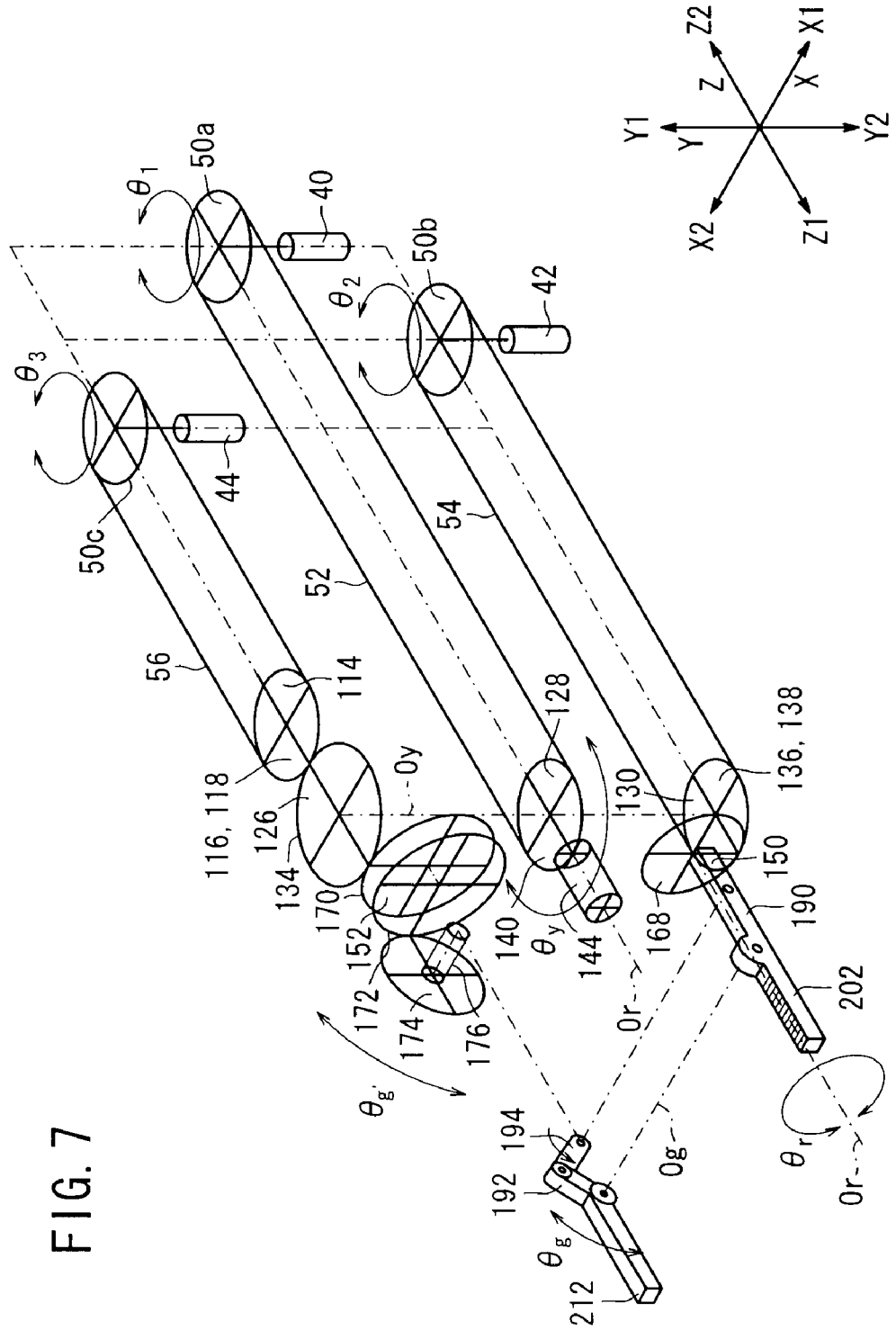
FIG. 7 is a basic schematic view of a driving system for the manipulator according to the first embodiment.

Next, operations of the manipulator 10a constructed in the foregoing manner shall be described below with reference to FIG. 7.

First, the manipulator 10a is actuated in a yawing direction by operating the first instruction lever 34 (see FIG. 1) with the finger. Specifically, when a surgeon handling the manipulator 10a operates the first instruction lever 34 with the finger, the motor 40 is energized to rotate the drive pulley 50a to circulatively drive the wire 52, thereby rotating the main axis member 128 centrally about the first rotational axis Oy. Owing thereto, the compound mechanism 102 and the end effector 104 that are connected to the support bar 144 of the main axis member 128 are made to swing in the yawing direction. In this manner, since movement in the yawing direction principally is carried out by the motor 40, the motor 40 is classified as a posture axis actuator. However, together with movement in the yawing direction, the motors 42 and 44 are cooperatively driven so as to maintain the postures of the gripper axis and the roll axis, or to bring them into a specified posture.

The first instruction lever 34 is tiltable selectively bidirectionally in both positive and reverse directions. Corresponding to the tilting direction of the first instruction lever 34, motions in the yawing direction are actuated by swinging in a positive direction or in a reverse direction. When the first instruction lever 34 is returned to a neutral position, the motor 40 is halted, thereby holding and stopping movement as well, at the position reached in the yawing direction at that moment.

The manipulator 10a is actuated in a rolling direction by operating the second instruction lever 36 (see FIG. 1) with the finger. Specifically, when a surgeon handling the manipulator 10a operates the second instruction lever 36 with the finger, the motor 42 is energized to rotate the drive pulley 50b to circulatively drive the wire 54, thereby rotating the gear body 130, the rotation of which is transmitted through the gear 138 and the face gear 168 to the drive base 150. The drive base 150 is rotated centrally about the second rotational axis Or. Owing thereto, the compound mechanism 102 and the end effector 104 are made to rotate in the rolling direction. In this manner, since movement in the rolling direction principally is carried out by the motor 42, the motor 42 is classified as a posture axis actuator. However, together with movement in the rolling direction, the motor 44 is cooperatively driven so as to maintain the posture of the gripper axis or to bring it into a specified posture.

The second instruction lever 36 is tiltable selectively bidirectionally in both positive and reverse directions. Corresponding to the tilting direction of the second instruction lever 36, motions in the rolling direction are actuated by rotating in a positive direction or in a reverse direction. When the second instruction lever 36 is returned to a neutral position, the motor 42 is halted, thereby holding and stopping movement as well, at the position reached in the rolling direction at that moment.

The end effector 104 is selectively opened and closed by pulling the trigger lever 32 (see FIG. 1) with the finger. Specifically, by pulling the trigger lever 32 with the finger, the motor 44 is energized to rotate the drive pulley 50c, thereby circulatively moving the wire 56 and rotating the gear body 114, the rotation of which is transmitted to the pin 176 through the gear 118, the gear 134, the face gears 170, 172, and the gear 174. The pin 176 causes the second end effector member 192 to swing centrally about the third rotational axis Og through the link 194. Accordingly, the second gripper 212 is opened away from or closed toward the first gripper 202. In this manner, since opening and closing movements of the end effector principally are carried out by the motor 44, the motor 44 is classified as an end effector axis actuator.

The trigger lever 32 is capable of being pulled by a finger, and returned to its original position by resiliency when the finger is released from the trigger lever 32. The end effector 104 operates in a ganged relation with the trigger lever 32, such that the end effector 104 is closed corresponding to the degree to which the trigger lever 32 is pulled, and is returned to an open condition when the trigger lever 32 is released. The trigger lever 32 may be combined with a latching mechanism, if so desired.

The above operations are carried out by the controller 45, while maintaining the rotational positions of the motor axes of motors 40, 42 and 44 at every minute time interval.

Next, an explanation shall be given of the functions and equations used for controlling the manipulator 10a. In the following explanations, $\theta_1$ indicates the rotation angle of the drive pulley 50a of the motor 40, $\theta_2$ indicates the rotation angle of the drive pulley 50b of the motor 42, and $\theta_3$ indicates the rotation angle of the drive pulley 50c of the motor 44. Further, $\theta_y$ indicates the angle of inclination of the yaw axis, $\theta_r$ indicates the angle of rotation of the roll axis, and $\theta_g$ indicates the opening/closing angle of the gripper axis. Further, $\tau_y$ indicates the torque on the yaw axis, $\tau_r$ indicates the torque on the roll axis, and $\tau_g$ indicates the torque on the gripper axis.

The gripper axis is operated through a toggle mechanism, which is inconvenient in terms of analysis thereof, and therefore, in place of the variables $\theta_g$ and $\tau_g$, the rotational angle $\theta_{g'}$ and torque $\tau_{g'}$ of the gear 174 are used below for analytical purposes. Because movements through the gripper axis and movements through the gear 174 correspond one to one, even when exchanged in this manner, clearly, there is no problem in terms of analysis. The angle $\theta_{g'}$ and the torque $\tau_{g'}$ shall also be referred to simply as the gripper axis angle and gripper axis torque below.

The relational expressions for the working unit posture axis angles $[\theta_y\ \theta_r\ \theta_{g'}]^T$ and the motor axis angles $[\theta_1\ \theta_2\ \theta_3]^T$, as well as the working unit posture axis torques $[\tau_y\ \tau_r\ \tau_{g'}]^T$ and the motor axis torques $[\tau_1\ \tau_2\ \tau_3]^T$ are represented by the following equations (1-1), (1-2) and (1-3). Herein, [A] is a 3-row, 3-column mechanical interference matrix determined by the compound mechanism 102, whereas $[A^T]^{-1}$ is a reverse matrix transposition of the matrix [A].

$$\begin{bmatrix} \theta_1 \\ \theta_2 \\ \theta_3 \end{bmatrix} = [A] \begin{bmatrix} \theta_y \\ \theta_r \\ \theta_{g'} \end{bmatrix} \quad (1\text{-}1)$$

$$\begin{bmatrix} \theta_y \\ \theta_r \\ \theta_{g'} \end{bmatrix} = [A]^{-1} \begin{bmatrix} \theta_1 \\ \theta_2 \\ \theta_3 \end{bmatrix} \quad (1\text{-}2)$$

$$\begin{bmatrix} \tau_1 \\ \tau_2 \\ \tau_3 \end{bmatrix} = [A^T]^{-1} \begin{bmatrix} \tau_y \\ \tau_r \\ \tau_{g'} \end{bmatrix} \quad (1\text{-}3)$$

The relationship of the posture axis angles $[\theta_y\ \theta_r\ \theta_{g'}]^T$ and the motor axis angles $[\theta_1\ \theta_2\ \theta_3]^T$ and torque is represented by equation (2). Herein, Rnn is a value that is determined by the reduction ratio of the pulley ratio, the number of gear teeth, etc.

$$\begin{bmatrix} \theta_1 \\ \theta_2 \\ \theta_3 \end{bmatrix} = \begin{bmatrix} R_{11} & R_{12} & R_{13} \\ R_{21} & R_{22} & R_{23} \\ R_{31} & R_{32} & R_{33} \end{bmatrix} \begin{bmatrix} \theta_y \\ \theta_r \\ \theta_{g'} \end{bmatrix} \quad (2)$$

To simplify understanding, when each of the reduction ratios is assumed to be 1, the aforementioned equations (1-1), (1-2) and (1-3) are represented by the following equations (3-1), (3-2) and (3-3).

$$\begin{bmatrix} \theta_1 \\ \theta_2 \\ \theta_3 \end{bmatrix} = \begin{bmatrix} 1 & 0 & 0 \\ 1 & -1 & 0 \\ -1 & -1 & 1 \end{bmatrix} \begin{bmatrix} \theta_y \\ \theta_r \\ \theta_{g'} \end{bmatrix} \quad (3\text{-}1)$$

$$\begin{bmatrix} \theta_y \\ \theta_r \\ \theta_{g'} \end{bmatrix} = \begin{bmatrix} 1 & 0 & 0 \\ 1 & -1 & 0 \\ 2 & -1 & 1 \end{bmatrix} \begin{bmatrix} \theta_1 \\ \theta_2 \\ \theta_3 \end{bmatrix} \quad (3\text{-}2)$$

$$\begin{bmatrix} \tau_1 \\ \tau_2 \\ \tau_3 \end{bmatrix} = \begin{bmatrix} 1 & 1 & 2 \\ 0 & -1 & -1 \\ 0 & 0 & 1 \end{bmatrix} \begin{bmatrix} \tau_y \\ \tau_r \\ \tau_{g'} \end{bmatrix} \quad (3\text{-}3)$$

Each of the axial torques upon gripping movement of the end effector 104 is investigated. The gripper axis torque required for gripping movement is provisionally set to $\tau_{g'}=1$. At this time, the ratios of the driving torques for each of the motors 40, 42, 44 are determined by substituting the values $\tau_y=0$, $\tau_r=0$ and $\tau_{g'}=1$ into equation (3-3).

$$\tau_1=2, \tau_2=-1, \tau_3=1 \quad (4)$$

These are the values that are shown by the third column of equation (3-3). In this manner, when a gripping movement occurs, and when a torque of $\tau_{g'}=1$ is generated by the third axis motor, as an interference torque, for the first axis motor 40, a torque which is two times the torque of the third axis motor 44 is required. Further, for the second axis motor 42, a torque, which is one times the torque of the third axis motor 44, is required. The second axis receives a reactive force of the third axis in accordance with the gripping movement, and then the first axis receives the sum of the reactive forces of the second axis and the third axis.

Figure 8:
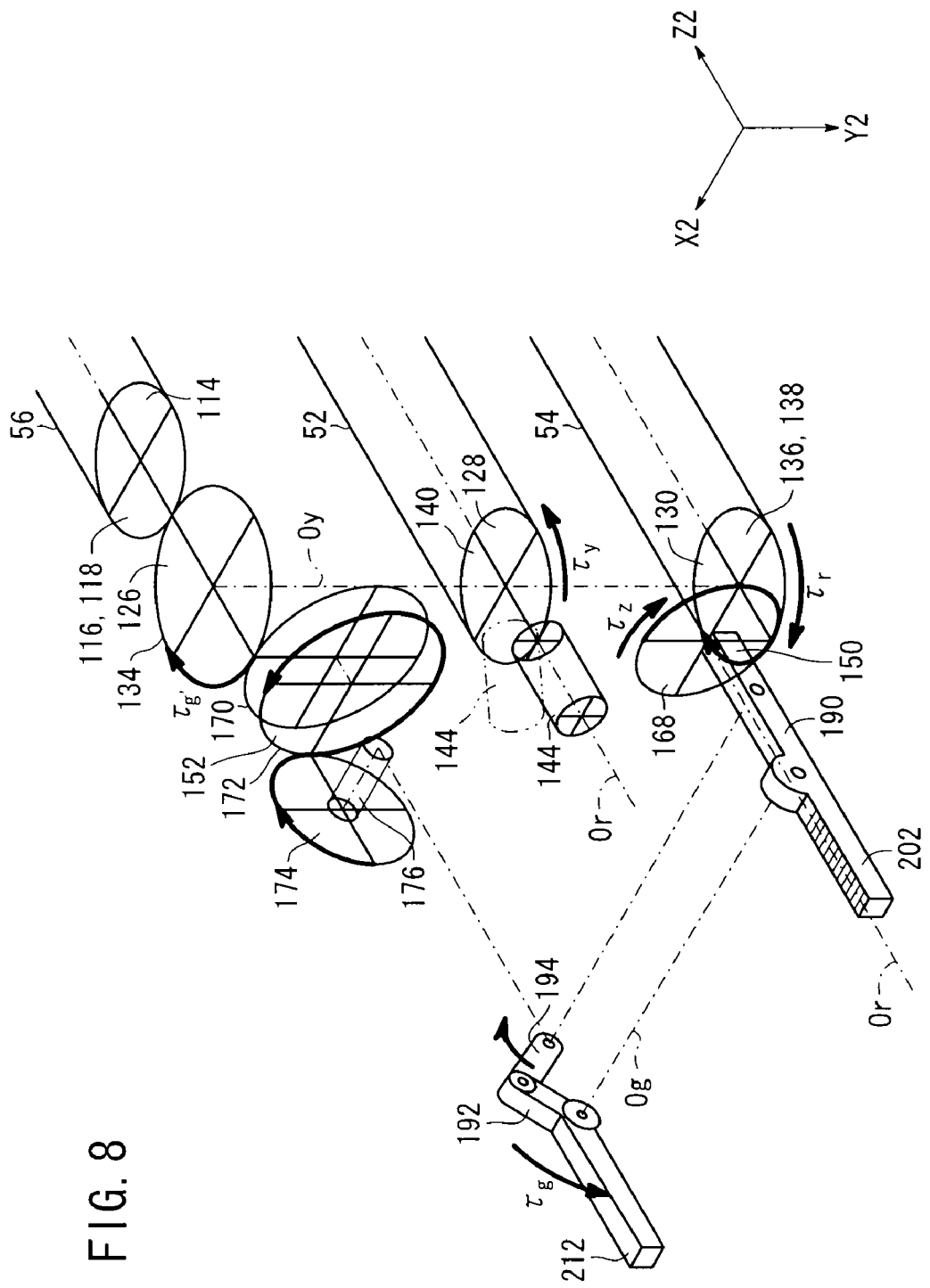
FIG. 8 is a schematic view showing a relationship between respective torques generated on the working unit of a manipulator according to the first embodiment.

As shown in FIG. 8 in outline form, when the second gripper 212 closes and abuts against the first gripper 202 and a pressing force is generated, the gear 174 causes torque to be generated in a clockwise direction in a side surface view (as viewed in the X2 direction), the face gear 172 causes torque to be generated in a counterclockwise direction in a frontal surface view (as viewed in the Z2 direction), and the gear 134 causes the torque $\tau_{g'}$ to be generated in a clockwise direction in plan view (as viewed in the Y2 direction).

When a torque for rotating the face gear 172 in a counterclockwise direction is generated, as a counter-reaction thereof, a torque $\tau_z$ is generated in a clockwise direction in frontal surface view at the face gear 168. Also, the torque $\tau_r$ is generated in a clockwise direction in plan view at the gear 138.

On the other hand, at the main axis member 128, the torque $\tau_{g'}$ of the gear 134 and the torque $\tau_r$ of the gear 138 are cumulatively added, and as a counter-reaction (interference torque) thereof, a torque $\tau_y$ ($=\tau_{g'}+\tau_r$) in a counterclockwise direction in plan view is generated, which is understood to result in unnecessary swinging motion of the support bar 144 in the opposite direction. Specifically, for causing the torque $\tau_g$ (i.e., the torque $\tau_{g'}$ at the gear 174) at the gripper axis by the motor 44, a torque $\tau_2$ sufficient to generate the torque $\tau_r$ on the gear 138 must be generated by the motor 42, and a torque $\tau_1$ sufficient to generate the torque $\tau_y$ on the main axis member 128 must be generated by the motor 40.

As a result, each of the wires is stretched (elongated) in proportion to each of the torques $\tau_1, \tau_2, \tau_3$ of the motors 40, 42, 44 and corresponding to its elasticity.

The stretching ratios of the wires of each of the drive systems are as shown below, assuming the rigidity of each of the wires to be equivalent.

$$\theta_1=2, \theta_2=-1, \theta_3=1 \qquad (5)$$

Consequently, for example, the support bar 144, which represents the yaw axis, in comparison to its original position, swings unnecessarily as shown by the two-dot-dash line in FIG. 8. In this way, the yaw and roll axes undergo unnecessary variations in posture upon elongation of the wires, so that a sense of uneasiness may be felt by the operator.

In order to prevent generation of unnecessary movements by such interference torques, for example, a thicker wire could be used for improving rigidity. However, if too thick a wire is used, the connecting shaft 48 through which the wire passes between the operating element and the working element must inevitably be made large in diameter as well.

In the event that elongation of the wires corresponding as above to each of the axes occurs, the amount of posture variation caused by elongation of the wires can be obtained by substituting the wire elongation amounts into equation (3-2), as follows.

$$\theta_y=2, \theta_r=3(=2+1), \theta_g=6(=4+1+1) \qquad (6)$$

In this manner, in a drive mechanism (i.e., a clamp, needle driver (needle forceps), grasping forceps, etc.) having three degrees of freedom made up of a yaw axis, a roll axis, and a gripper axis, if left as is, the wires apart from the drive axis become elongated as a result of interference torques, and variations in posture cannot be avoided.

Consequently, in the manipulator 10a, in order to compensate for such variations, the controller 45 carries out a compensating control for the motors 40, 42, and 44. The configuration of the controller 45 shall now be described below.

Figure 9:
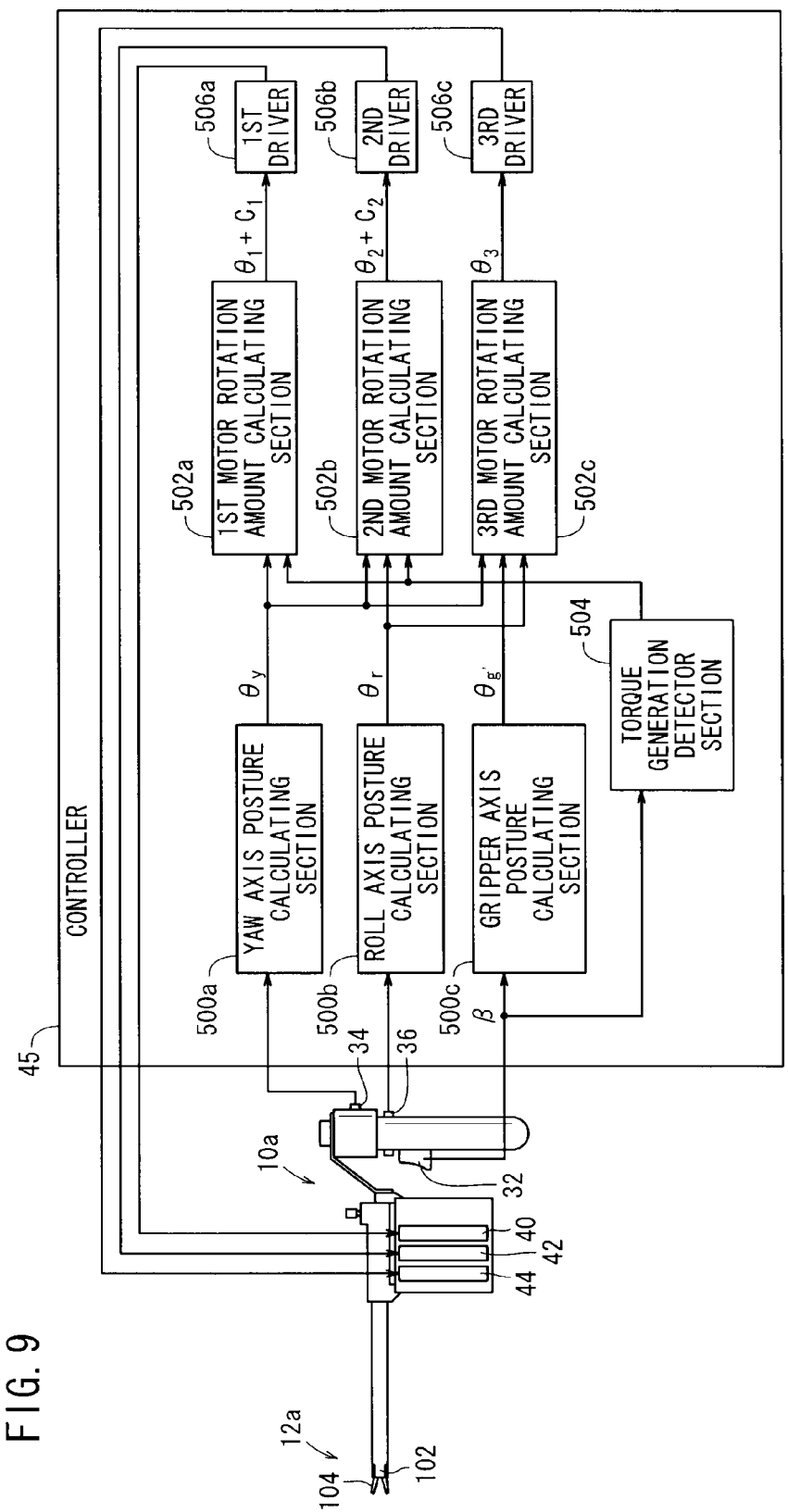
FIG. 9 is a structural block diagram of a controller.

As shown in FIG. 9, the controller 45 includes a yaw axis posture calculating section 500a, a roll axis posture calculating section 500b, and a gripper axis posture calculating section 500c. The yaw axis posture calculating section 500a calculates the yaw axis angle $\theta_y$ based on operation of the first instruction lever 34, while the roll axis posture calculating section 500b calculates the roll axis angle $\theta_r$ based on operation of the second instruction lever 36. The yaw axis posture calculating section 500a and the roll axis posture calculating section 500b calculate the yaw axis angle $\theta_y$ and the roll axis angle $\theta_r$, for example, by integrating operations in plus and minus directions of the first instruction lever 34 and the second instruction lever 36. The gripper axis posture calculating section 500c calculates the gripper axis angle $\theta_g$ and the angle $\theta_{g'}$ of the gear 174 based on the amount at which the trigger lever 32 is pulled.

Further, the controller 45 has a first motor rotation amount calculating section 502a, a second motor rotation amount calculating section 502b, a third motor rotation amount calculating section 502c, a torque generation detector section 504, along with a first driver 506a, a second driver 506b, and a third driver 506c.

The first motor rotation amount calculating section 502a calculates the rotation amount $\theta_1$ of the motor 40 based on the yaw axis angle $\theta_y$. The second motor rotation amount calculating section 502b calculates the rotation amount $\theta_2$ of the motor 42 based on the yaw axis angle $\theta_y$ and the roll axis angle $\theta_r$. The third motor rotation amount calculating section 502c calculates the rotation amount $\theta_3$ of the motor 44 based on the yaw axis angle $\theta_y$, the roll axis angle $\theta_r$ and the gripper axis angle $\theta_{g'}$. The first motor rotation amount calculating section 502a, the second motor rotation amount calculating section 502b, and the third motor rotation amount calculating section 502c, include functions that correspond basically to the aforementioned equation (3-1). The first motor rotation amount calculating section 502a and the second motor rotation amount calculating section 502b, additionally, include functions for correcting each of the rotation amount $\theta_1$ and the rotation amount $\theta_2$ based on signals supplied from the torque generation detector section 504. The functions will be described later on.

Figure 10:
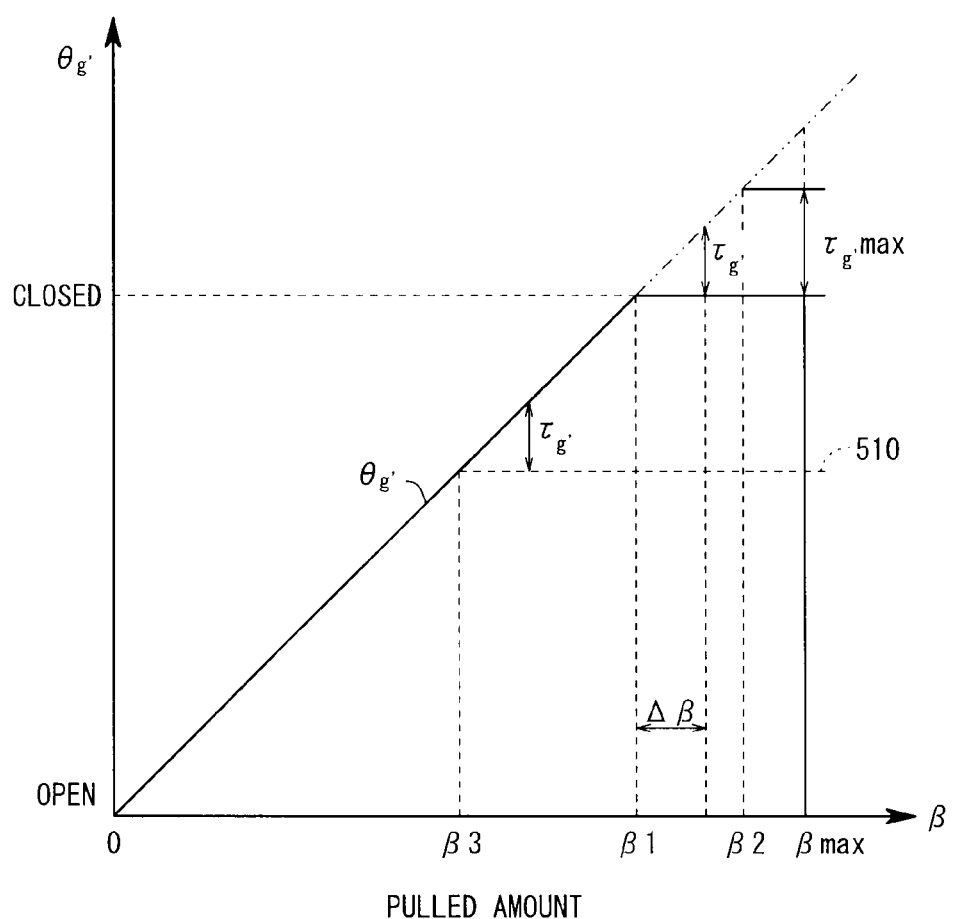
FIG. 10 is a graph illustrating relationships between a gripper torque, a trigger pull amount, and a degree of opening of the gripper.

As shown in FIG. 10, the gripper axis posture calculating section 500c sets the gripper axis angle $\theta_{g'}$ proportionally with respect to a range from the minimum value 0 of the pulled amount $\beta$ of the trigger lever 32 to the maximum value $\beta$max thereof. However, the movement ranges of the gripper axis corresponds to $0 \leq \beta < \beta 1$, wherein a closed state results within the range $\beta \geq \beta 1$, and a deviation occurs between the command value and the actual posture, such that the torque $\tau_{g'}$ is generated corresponding to such a deviation.

The torque $\tau_{g'}$ basically increases corresponding to the deviation. However, within a range in which the pulled amount $\beta$ is equal to or greater than a predetermined amount $\beta 2$, a torque value equal to or above a predetermined torque $\tau_{g'}$max cannot be generated depending on the capacity of the motor 44 and the rigidity of the wire 56, etc., so that the torque $\tau_{g'}$ is limited to the value thereof.

Even within the range of $\beta < \beta 1$, the gripper axis generates a minute torque so as to overcome friction and the like, however this torque is sufficiently small compared to the gripping torque $\tau_{g'}$ generated within the range $\beta \geq \beta 1$, so that it can be ignored analytically.

The torque generation detector section 504 makes up a torque generation detection means, which detects a timing at which the gripping torque $\tau_{g'}$ is generated based on the pulled amount $\beta$ of the trigger lever 32, that is, a timing wherein the pulled amount $\beta$ is such that $\beta \geq \beta 1$ in which the pulled amount $\beta$ has reached the amount $\beta 1$ corresponding to the end of the movement range.

In addition, the torque generation detector section 504, at the timing $\beta \geq \beta 1$, also calculates an excess amount $\Delta \beta$ ($=\beta - \beta 1$) with respect to the standard value $\beta 1$, which is supplied to the first motor rotation amount calculating section 502a and the second motor rotation amount calculating section 502b. Further, within the range of $\beta \geq \beta 2$, the excess amount $\Delta \beta$ may also be limited to $\Delta \beta = \beta 2 - \beta 1$.

The torque generation detector section 504 may also perform processing based not on a pulled amount $\beta$, but rather based on the gripper axis angle $\theta_{g'}$ which is obtained from the gripper axis posture calculating section 500c.

Further, in the event that the gripper axis is used for gripping a somewhat large workpiece, a torque $\tau_{g'}$ that is generated from a predetermined value $\beta 3$ ($\beta 3 < \beta 1$) before the condition $\beta = \beta 1$ occurs, may also be considered (refer to the broken line 510 in FIG. 10). In order to apply this technique more suitably, rather than using the pulled amount $\beta$, the torque generation detector section 504 may also detect the timing based on the current amount at which the motor 44 is driven.

Figure 11:
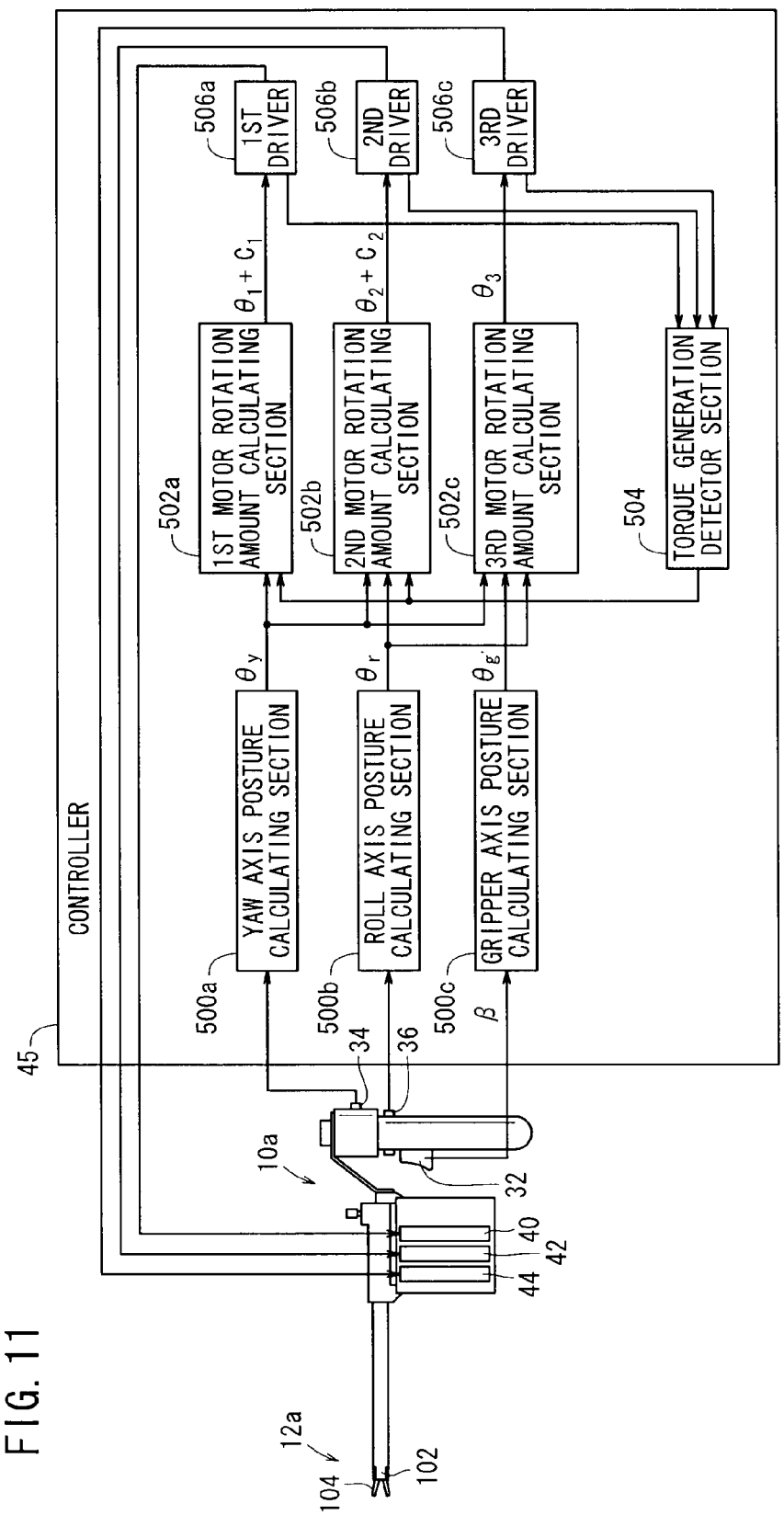
FIG. 11 is a structural block diagram of a controller according to a first modification.

More specifically, as shown in FIG. 11, the third driver 506c supplies the current value for driving the motor 44 to the torque generation detector section 504. In the torque generation detector section 504, when the obtained current value becomes equal to or more than a predetermined threshold, the timing at which the torque $\tau_{g'}$ is generated on the gripper axis is determined, whereupon a predetermined command may be given to the first motor rotation amount calculating section 502a and the second motor rotation amount calculating section 502b.

Furthermore, by means of a given sensor, the angle $\theta_3$ corresponding to the angle command with respect to the motor 44 may also be detected along with the actual angle $\theta_{3S}$ of the rotation axis of the motor 44 or of the drive pulley 50c connected to the rotation axis of the motor 44, whereby the timing is detected based on the deviation between the angle $\theta_3$ and the actual angle $\theta_{3S}$.

Figure 12:
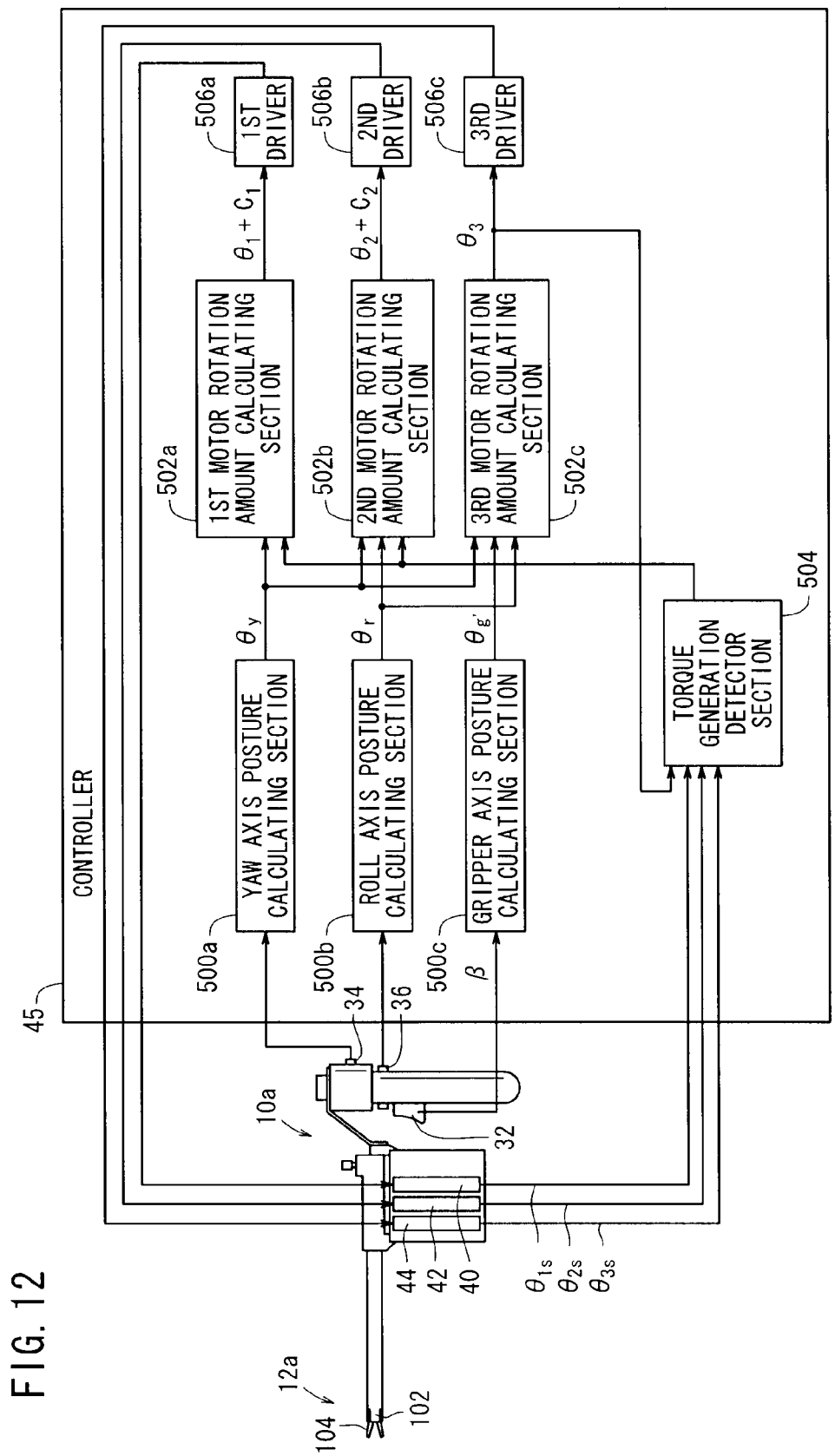
FIG. 12 is a structural block diagram of a controller according to a second modification.

More specifically, as shown in FIG. 12, respective actual angles $\theta_{1S}, \theta_{2S}, \theta_{3S}$ obtained by given sensors from the motors 40, 42, 44 and the command angle $\theta_3$ set by the third motor rotation amount calculating section 502c are supplied to the torque generation detector section 504. In the torque generation detector section 504, the deviation between the command angle $\theta_3$ and the actual angle $\theta_{3S}$ is determined, and when the deviation becomes equal to or more than a predetermined threshold, the timing at which the torque $\tau_{g'}$ is generated on the gripper axis is determined, whereupon a predetermined command may be given to the first motor rotation amount calculating section 502a and the second motor rotation amount calculating section 502b.

Since there is a roughly proportional correlation between the torque $\tau_{g'}$ and the current value or deviation, it is also possible to detect the timing at which the torque $\tau_{g'}$ is generated by means of the aforementioned current value.

Next, in the first motor rotation amount calculating section 502a and the second motor rotation amount calculating section 502b, the rotation amounts $\theta_1$ and $\theta_2$ are corrected by the following procedure based on the excess amount $\Delta\beta$ supplied from the torque generation detector section 504. For the sake of convenience, the processing in the first motor rotation amount calculating section 502a and in the second motor rotation amount calculating section 502b shall be described together. The processing performed by these elements is carried out continuously at every minute time interval.

Figure 13:
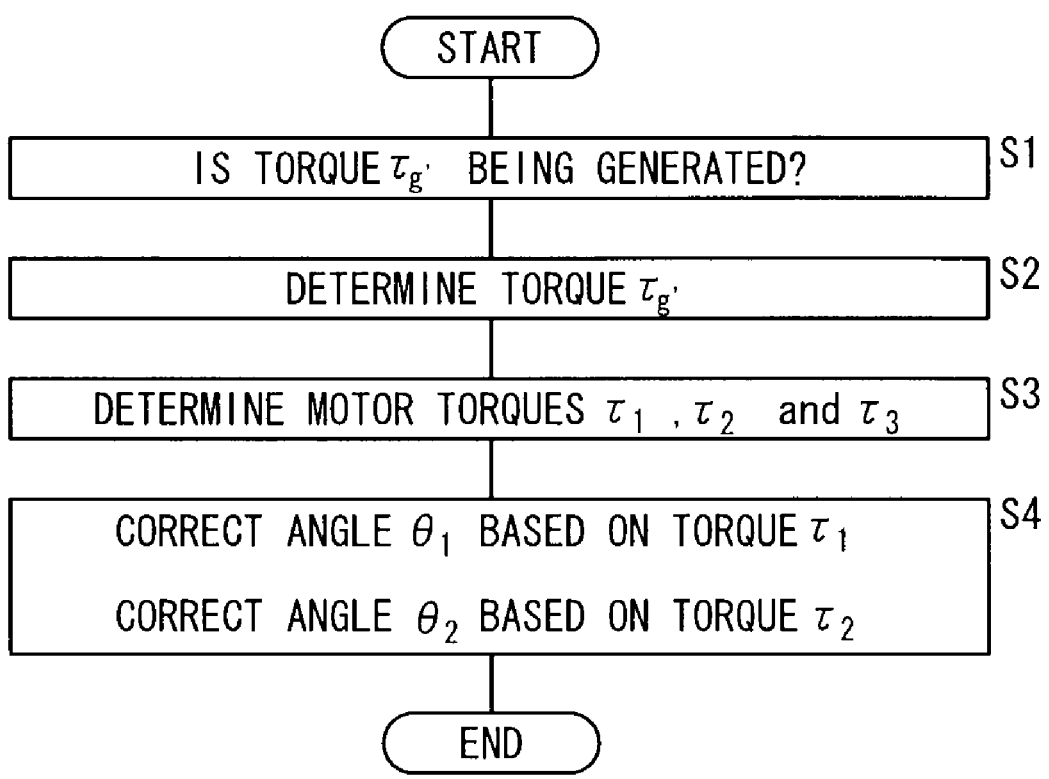
FIG. 13 is a flowchart of a control sequence carried out by a controller.

First, in step S1 of FIG. 13, the torque generation detector section 504 determines whether or not the torque $\tau_{g'}$ is being generated based on the pulled amount $\beta$. When it is judged that the torque $\tau_{g'}$ is being generated (i.e., when $\beta \geq \beta 1$), the excess amount $\Delta\beta$ is supplied to the first motor rotation amount calculating section 502a and the second motor rotation amount calculating section 502b.

In step S2, the first motor rotation amount calculating section 502a and the second motor rotation amount calculating section 502b determine the gripper axis torque $\tau_{g'}$ based on the excess amount $\Delta\beta$, and based on a proportionality relation or a predetermined relational expression. For simplicity, the first motor rotation amount calculating section 502a and the second motor rotation amount calculating section 502b may receive just the timing at which the torque $\tau_{g'}$ is generated, from the torque generation detector section 504, wherein the torque $\tau_{g'}$ is treated as $\tau_{g'} = \tau_{g'}$max (see FIG. 10). This is because, during the actual procedure, it is frequently the case that the trigger lever 32 is pulled until reaching the maximum pull-in amount thereof, at which $\beta = \beta$max.

In step S3, the torque $\tau_{g'}$ is substituted in the above-noted equation (3-3) and the torques $\tau 1$, $\tau 2$ and $\tau 3$ generated by the motors 40, 42, 44 are determined. At this time, $\tau_y$ and $\tau_r$ are set such that $\tau_y = \tau_r = 0$. According to equation (3-3), $\tau_1 = 2 \cdot \tau_{g'}$, $\tau_2 = -1 \cdot \tau_{g'}$, and $\tau_3 = \tau_{g'}$. Of course, strictly speaking, the reduction ratios of the mechanisms are not precisely 1, and thus the proportionality constants thereof become different values as represented by the combination of the Rnn values of equation (2).

In step S4, the angle $\theta_1$ that forms the angle command of the motor 40 is corrected based on the determined value $\tau_1$, and the angle $\theta_2$ that forms the angle command of the motor 42 is corrected based on the determined value $\tau_2$.

Figure 14A:
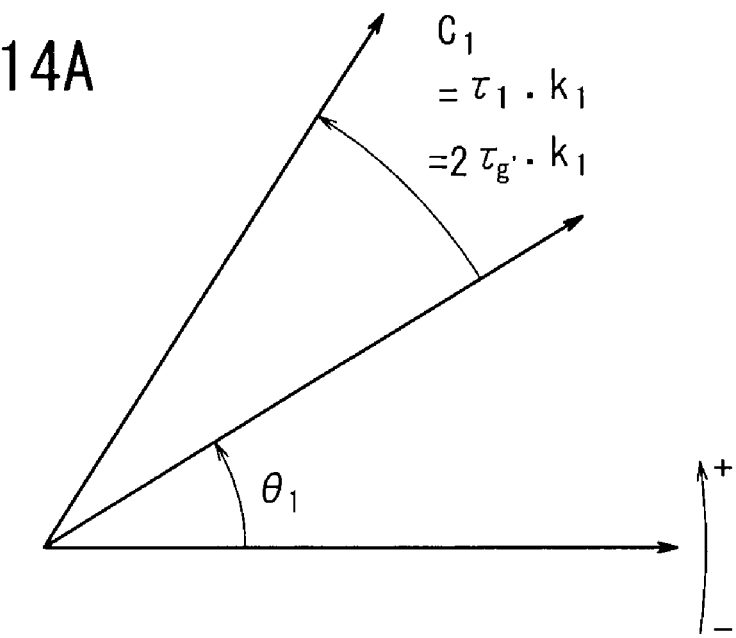
FIG. 14A is a view showing a manner of correcting an angle of a first axis.

More specifically, as shown in FIG. 14A, an angle $(\theta_1 + C_1)$ is determined, i.e., a correction amount $C_1$ proportional to $\tau_1$ ($= 2 \cdot \tau_{g'}$) is added with respect to the angle $\theta_1$ at that point in time, and is supplied to the first driver 506a. In this case, from the fact that $\tau_1$ is a positive value, a correction results in which the angle $\theta_1$ increases.

Figure 14B:
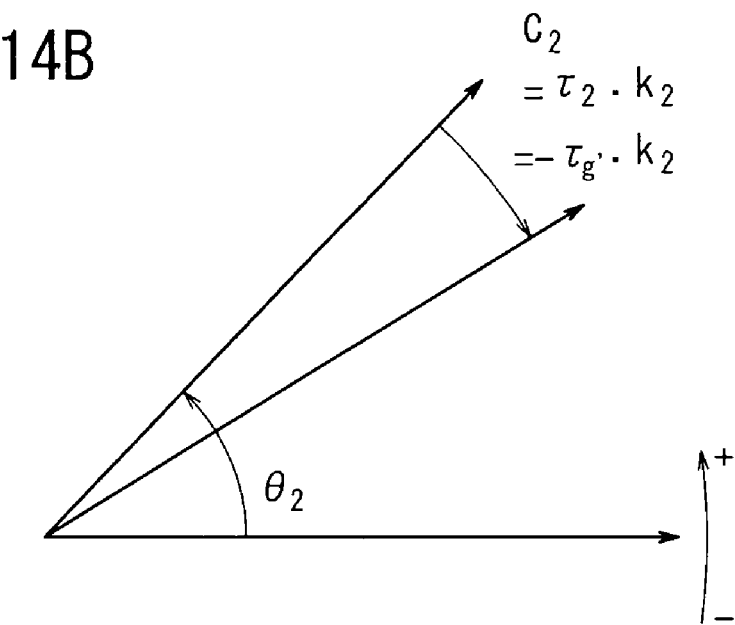
FIG. 14B is a view showing a manner of correcting an angle of a second axis.

Further, as shown in FIG. 14B, an angle $(\theta_2 + C_2)$ is determined, i.e., a correction amount $C_2$ proportional to $\tau_2$ ($= -1 \cdot \tau_{g'}$) is added with respect to the angle $\theta_2$ at that point in time, and is supplied to the second driver 506b. In this case, from the fact that $\tau_2$ is a negative value, a correction results in which the angle $\theta_2$ decreases. That is, a control is performed in which the target position is shifted in the same direction as the direction generated by the interference torque.

The angle $\theta_3$ at that point in time is not corrected, but may be supplied as is, to the third driver 506c.

The proportionality coefficient $k_1$ between the torque $\tau_1$ and the correction amount $C_1$ may be determined such that the posture variation amount of the yaw axis due to generation of the torque $\tau_1$ by the motor 40 matches the correction amount $C_1$. Elongation of the wire 52 also is considered in the proportionality coefficient $k_1$. In the same manner, the proportionality coefficient $k_2$ between the torque $\tau_2$ and the correction amount $C_2$ may be determined such that the posture variation amount of the roll axis due to generation of the torque $\tau_2$ by the motor 42 matches the correction amount $C_2$. Elongation of the wire 54 also is considered in the proportionality coefficient $k_2$.

The proportionality coefficients $k_1$ and $k_2$ are determined by computational simulations, experimentation, or the like. Further, the relationship between the torque $\tau_1$ and the correction amount $C_1$, as well as the relationship between the torque $\tau_2$ and the correction amount $C_2$, are not necessarily restricted to being a proportional relation. For example, a quadratic or higher order relational expression, or other experimental formulas, may also be adopted.

In this manner, by imparting the angle command $(\theta_1 - C_1)$ to the first driver 506a, the motor 40 is advanced so as to approximately reach the position of the angle $(\theta_1 - C_1)$, which is smaller than the original command angle $\theta_1$ (see FIG. 14A). On the other hand, in the motor 40, from the fact that the torque $\tau_1$ is generated in a positive direction as an interference torque for the purpose of the gripper axis generating the torque $\tau_{g''}$, elongation or warping occurs on the wire 52, while shifting occurs in the correspondence relation between the angles of the drive pulley 50a of the motor 40 and the main axis member 128, such that as a result, the yaw axis acquires a value which is extremely close to the angle $\theta_y$ that defines the initial target value.

Further, by imparting the angle command $(\theta_2 - C_2)$ to the second driver 506b, the motor 42 is advanced so as to approximately reach the position of the angle $(\theta_2 - C_2)$, which is greater than the original command angle $\theta_2$ (see FIG. 14B). On the other hand, in the motor 42, from the fact that the torque $\tau_2$ is generated in a negative direction as an interference torque for the purpose of the gripper axis generating the torque $\tau_{g''}$, elongation or warping occurs on the wire 54, while shifting occurs in the correspondence relation between the angles of the drive pulley 50b of the motor 42 and the gear 138, such that as a result, the roll axis acquires a value which is extremely close to the angle $\theta_r$ that defines the initial target value.

In this manner, in accordance with the manipulator 10a and control method therefor of the first embodiment, by means of the controller 45, the torque detector section 504 detects the timing at which the gripper axis torque $\tau_g$, is generated, and based on an excess amount $\Delta\beta$ that defines the detection signal, and taking as a standard the angles $\theta 1$, $\theta 2$ at the current positions the posture axes, a correction of the command signal in the same direction as the directions of the interference torques $\tau_1$, $\tau_2$ is carried out. Owing thereto, with the manipulator 10a, the appropriate three degrees of freedom can be attained when performing laparoscopic surgery, and even if elongation or warping of the wires 52, 54 occurs due to generation of the torque $\tau_g$, on the gripper axis, almost no unnecessary motion takes place on the other axes.

Accordingly, surgery can be performed without the operator experiencing any sense of uneasiness. Further, as a result of compensating the elongation on each of the wires, it becomes possible to use thin or narrower wires, whereby the connector 16 and the trocar 20 (see FIG. 1) can be set with narrow diameters.

Further, the two axes are provided as posture axes that change the inclination of the end effector 104, for which the size and direction of the interference torques ($\tau_1$ and $\tau_2$) generated thereby differ from each other. However, by means of the controller 45, based on calculated values of the generated interference torques, a control is carried out for shifting the movement positions of the motors 40 and 42 by the differing amounts on each of the posture axes. Accordingly, a suitable compensation control is enabled on each of the posture axes.

Further, the control method carried out by the controller 45 can be suitably enabled with respect to a manipulator having basically any type of structure, simply by modifying equations (2), (3-1) to (3-3), as well as the proportionality coefficients $k_1$ and $k_2$, according to the given mechanism.

Next, a manipulator 1ob according to a second embodiment shall be described. When describing the manipulator 10b (as well as the later-mentioned manipulator 10c), elements thereof which are the same as those of the manipulator 10a shall be designated using the same reference characters, and detailed descriptions of such features shall be omitted.

As shown in FIGS. 15 to 18, at the working unit 12b of the manipulator 10b, the gear body 126, the gear body 300, the main axis member 128 and the gear body 130, are axially supported in succession with respect to the shaft 112, from the Y1 direction toward the Y2 direction.

On the gear body 126, the portion thereof corresponding to the region 132a (see FIG. 5) is set thinly in profile.

In place of the aforementioned tubular member 140, a thin protective plate 171 is provided on the main axis member 128. The protective plate 171 is equipped with a central hole 171b therein through which the shaft 112 is inserted. The protective plate 171 has a roughly 90° circular arc shape in the Z2 direction, expands in the Z1 direction, and is substantially in the shape of a chevron when viewed in plan.

Figure 18:
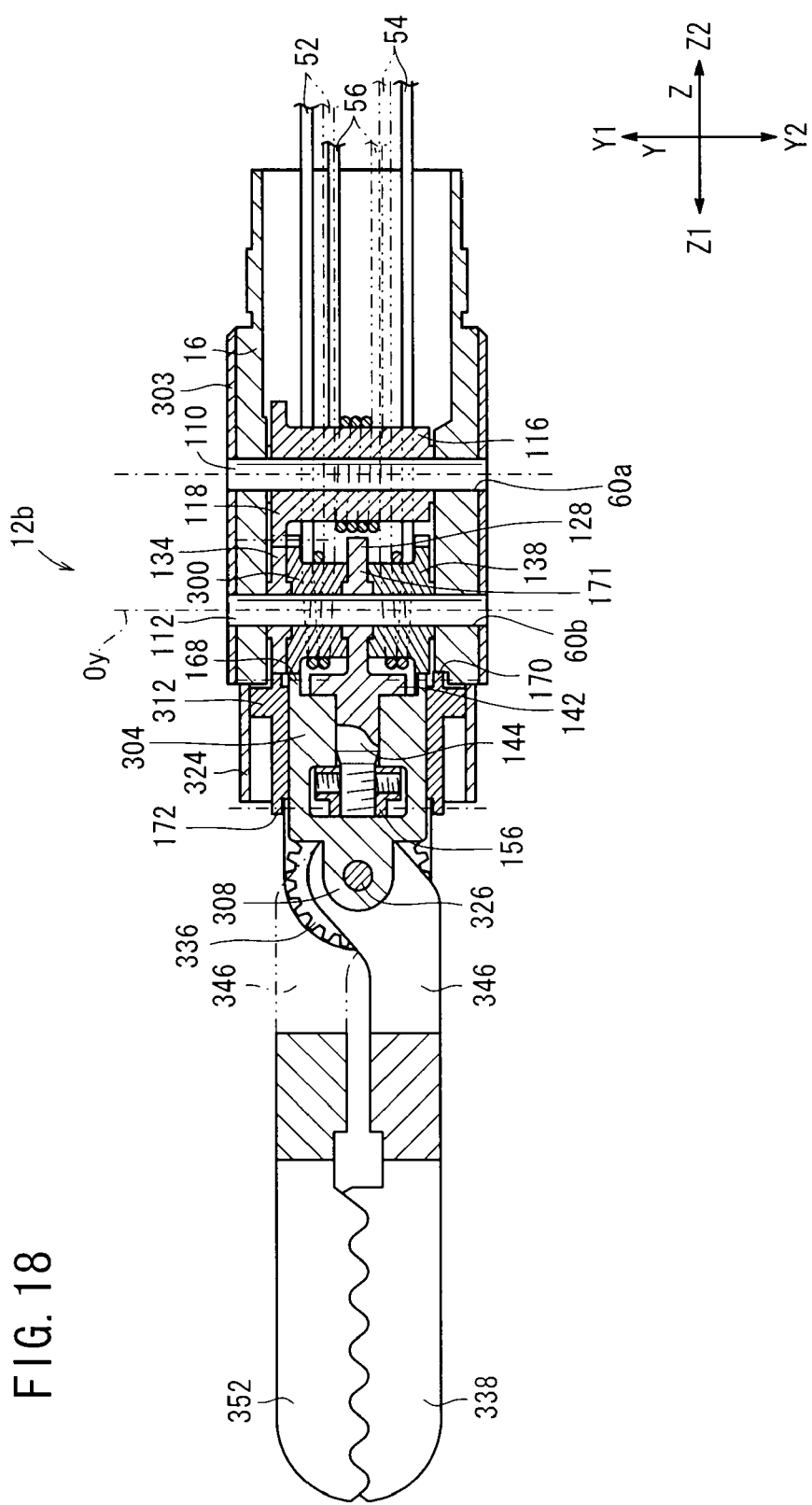
FIG. 18 is a cross sectional side view of the working unit in the manipulator according to the second embodiment.
Figure 19:
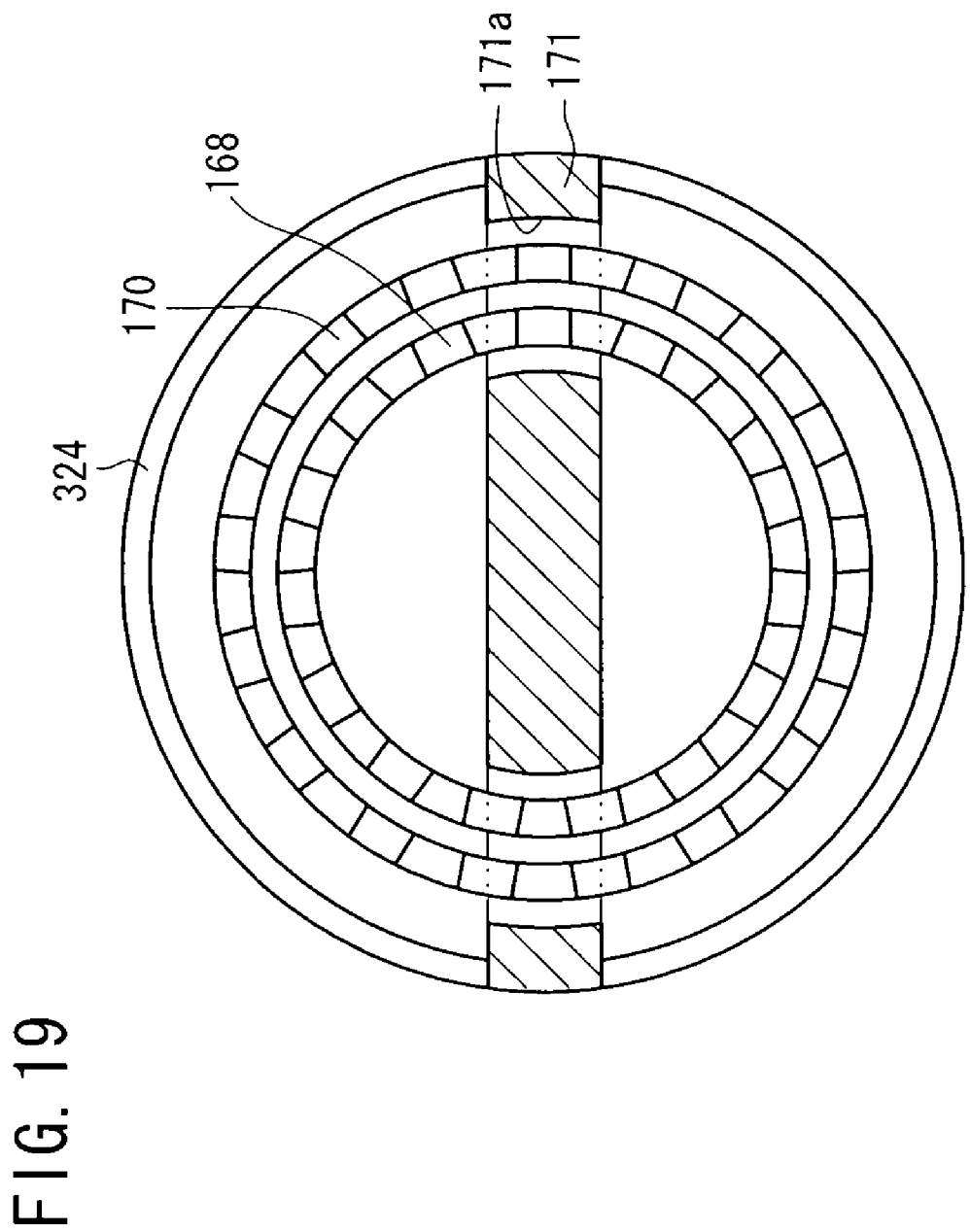
FIG. 19 is a schematic cross sectional frontal surface view showing a positional relationship between a plate body of a main axis member and a gear.

As shown in FIGS. 18 and 19, when viewed in plan (stated otherwise, when projected in the axial direction), the protective plate 171 covers the gear 134, the gear 301 and the gear 138. Further, the teeth of the face gear 168 and the face gear 170 are inserted into a recess 171a provided in the end surface facing the Z1 direction. Accordingly, the gear teeth do not contact a thread or the like that is used for performing a tie-knot operation, the thread is not drawn therein, and entanglement or interference with the gear teeth can be prevented.

Figure 20:
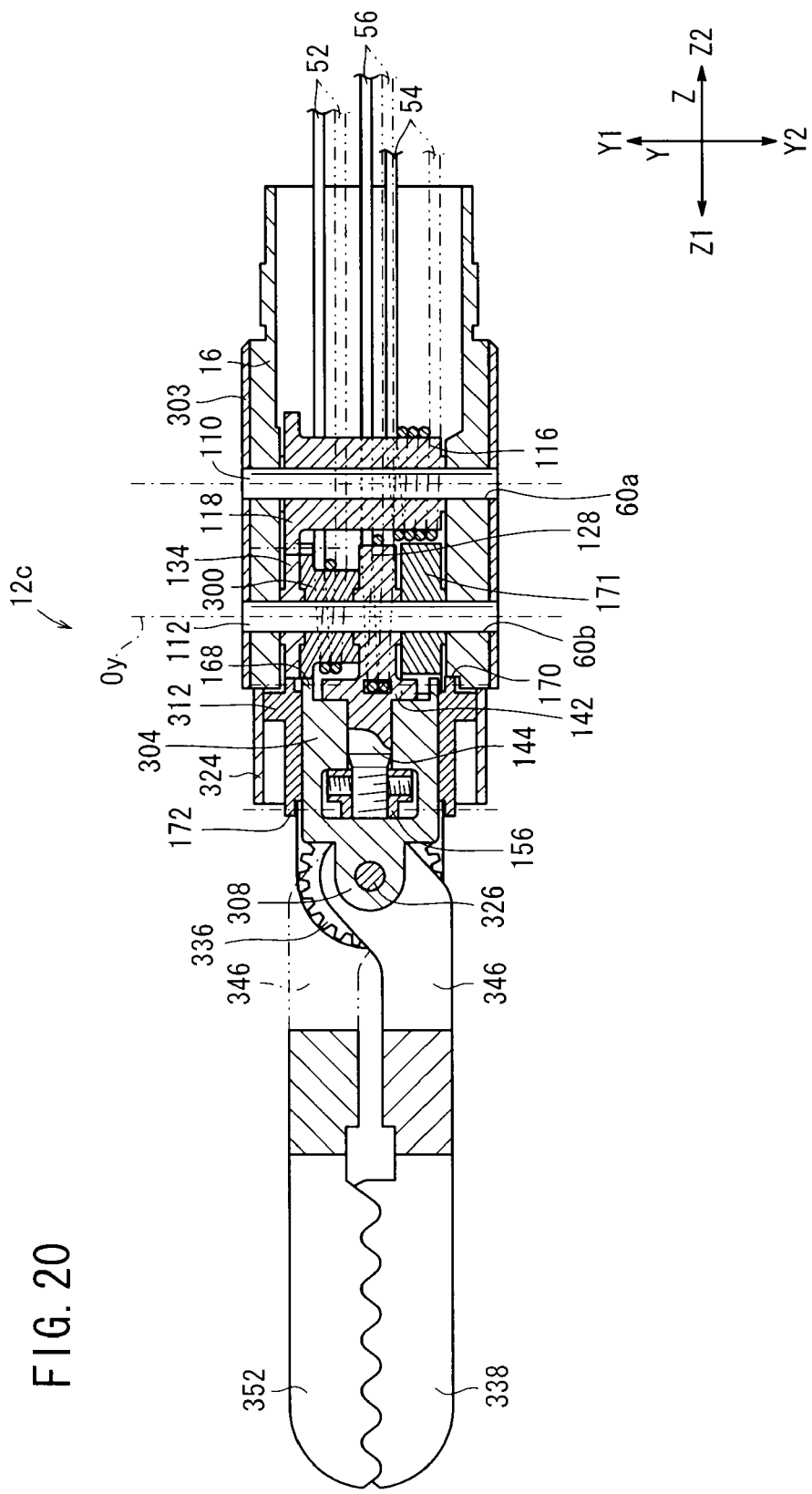
FIG. 20 is a cross sectional side view of a working unit in a manipulator equipped with an independent plate body.
Figure 21:
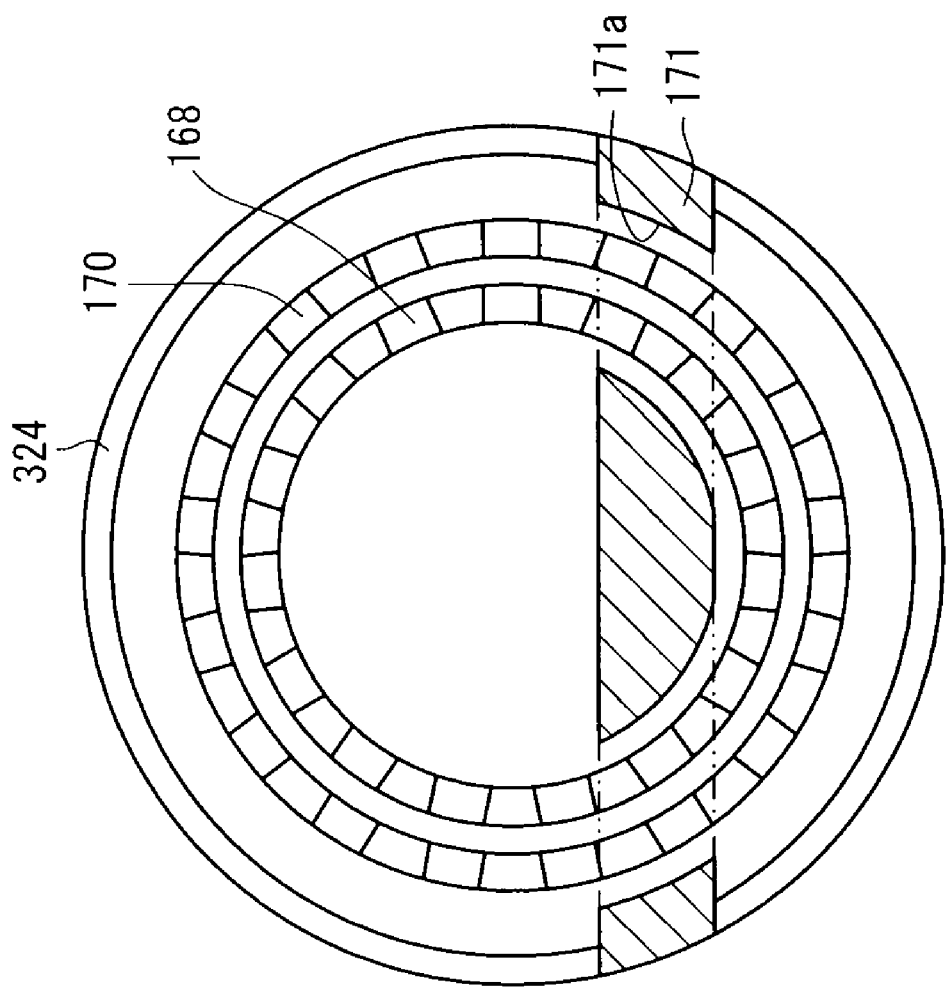
FIG. 21 is a schematic cross sectional frontal view showing a positional relationship between an independent plate body and a gear.

It is not essential that the protective plate 171, which acts as a member for preventing entanglement or interference of threads, etc., be constructed integrally with the main axis member 128. For example, as shown in FIGS. 20 and 21, the protective plate 171 may be disposed separately from the main axis member 128, underneath the main axis member 128 (in the Y2 direction).

In this manner, as a result of the protective plate 171 being disposed so as to cover at least a portion of the face gears 168 and 170, entanglement of threads or the like in the face gears 168 and 170 can be prevented. In particular, the protective plate 171 has a shape that becomes narrower toward the rearward direction and thus the protective plate 171 does not hinder movement in the yaw axis direction, and threads or the like are not unnecessarily drawn into the face gears 168 and 170 or the gear 134, such that entanglement or interference with the face gears 168, 170 and the gear 134 can more reliably be prevented.

Further, since the protective plate 171 acts to cover the gear 134, the gear 301 and the gear 138 when viewed in plan, entanglement of threads or the like within these respective gears can also be prevented.

Returning to FIGS. 15 through 18, a cover 303 is installed on the working unit 12b for covering the tongues 58, the gear body 114, the gear 118, the gear 301 and the gear 138, and thus by this structure, entanglement of threads or the like therein can more reliably be prevented. As made clear from FIG. 17, taking as a standard the position of the shaft 112, the frontal portions of the protective plate 171 and the cover 303 have roughly symmetrical configurations, such that the protective plate 171 prevents entanglement of threads at a region primarily in the Z1 direction, whereas the cover 303 prevents entanglement or interference of threads at a region primarily in the Z2 direction.

The gear body 300 has the same structure as the gear body 130 while being arranged in a reverse direction. A gear 301 is provided on the gear body 300 in the same fashion as the gear 138. The wire 52 is wound around the tubular member 302 of the gear body 300. That is, driving by the motor 40 and the drive pulley 50a does not take place on the main axis member 128 itself, but rather, on the gear body 300.

The drive base (driven rotating body) 304 corresponds to the aforementioned drive base 150 and includes a face gear 168 disposed on an end surface thereof in the Z2 direction. The gear (first driving rotating body) 301 meshes with a top portion in the Y1 direction of the face gear 168, whereas the gear (second driving rotating body) 138 meshes with a top portion in the Y2 direction of the face gear 168, thereby constituting a so-called differential mechanism.

A space portion 306, which serves as a space for a fastening nut 156 to be threaded onto the support bar 144, is disposed at a central portion of the drive base 304, whereas a gripper base 308 serving as a base for opening and closing motions of the gripper is disposed on an end portion thereof in the Z1 direction. The gripper base 308 includes a pair of parallel lateral sliding surfaces 308a corresponding to the opening and closing orientations of the gripper, and a hole 308b, which forms a center of rotation, disposed on the end of the gripper base 308.

A gear ring (extension axis rotor) 310 corresponds to the aforementioned gear ring 152, and includes a face gear 170 on the end surface thereof in the Z2 direction, and another face gear 172 on the end surface thereof in the Z1 direction. The gear ring 310 is fitted over the tubular member 164 of the drive base 304. The gear ring 310 is somewhat longer than the aforementioned gear ring 152, and has an annular projection 312 disposed on its outer circumferential surface, offset slightly from the center toward the Z2 side thereof. A top portion in the Y1 direction of the face gear 170 meshes with the gear 134.

The end effector 104 comprises a first end effector body 320, a second end effector body 322, a cover 324 and a fixing pin 326. The fixing pin 326 is arranged and oriented along the third rotational axis Og.

The cover 324 is a member that both protects and supports the various components on the end effector 104. The cover 324 includes a short tube 330 extending in the Z2 direction, and a pair of ears 332 that project in the Z1 direction, from respective upper and lower end portions of the short tube 330. Holes 332a are provided on each of the ears 332 through which a fixing pin 326 is inserted and secured in place.

The first end effector body 320 includes a gear body 336 and an operating element 338. The gear body 336 is arranged in the X2 direction between the pair of ears 332, and includes a gear 340 and a projection 342 cut in a D-shape and projecting toward the X1 direction from the center of the gear 340. A hole 336a through which the fixing pin 326 is inserted is provided in a center portion of the gear body 336. The gear 340 of the gear body 336 is arranged in the X2 direction, such that the gear 340 meshes with a top portion in the X2 direction of the face gear 172.

The operating element 338 includes a base end cylinder 344, an arm 346 that project in a roughly radial direction from the base end cylinder 344, and a gripper 348, which projects even further in the radial direction from the arm 346. A D-cut shaped hole 344a suitable for engagement therein of the projection 342 is disposed in the center of the base end cylinder 344, which function both to position and stop relative rotation with respect to the projection 342.

The gripper 348 is somewhat wider in the X1 direction than the base end cylinder 344 and the arm 346, while a line with which the width of the gripper 348 is bisected, is substantially aligned with the end face in the X1 direction of the base end cylinder 344 and the arm 346. A wavy portion, which extends in the X direction in a circular arc shape at both ends on the inner side surface 348a, is provided on the gripper 348, which serves to prevent slippage of the gripped workpiece. Recesses 348b are also provided on the gripper 348.

The second end effector body 322 includes a gear body 350 and an operating element 352. The operating element 352 includes a gripper 353 having the same shape as the gripper 348. The gear body 350 is arranged in the X1 direction between the pair of ears 332, and includes a gear 354. The gear body 350 is positioned with the gear 354 thereof facing in the X1 direction, such that the gear 354 meshes with a top portion in the X1 direction of the face gear 172. Otherwise, the gear body 350 has the same shape as the gear body 336, and the gear 354 thereof corresponds to the gear 340. Other parts thereof are designated with the same reference numerals and detailed descriptions of such features shall be omitted.

The operating element 352 has the same shape as the operating element 338 and is engaged with the gear body 350. The operating element 352 is arranged in a vertically inverse orientation with respect to the operating element 338. Respective parts of the operating element 352 are designated with the same reference numerals as those of the operating element 338, and detailed descriptions of such features shall be omitted.

The gripper 348 of the first end effector body 320 is arranged on the Y2 direction side, whereas the gripper 353 of the second end effector body 322 is arranged on the Y1 direction side. The grippers 348 and 353 are positioned symmetrically about a standard axis C such that the inner side surfaces 348a thereof face each other. The standard axis C is coincident with the extension axes of the connecting shaft 48 and the working unit 12b.

The gear body 336, the gripper base 308 and the gear body 350 are arranged between the pair of ears 332 substantially without gaps. A fixing pin 326 is inserted through and axially supported by the hole 332a, the hole 308b, and the other hole 332a.

In the end effector 104, under a rotating action of the gear ring 310, the gear 340 and the gear 354 are rotated in mutually opposite directions. That is, as observed from the front surface, when the gear ring 310 rotates in a clockwise direction, in a side surface view (i.e., as viewed in the X2 direction), the gear 340 is rotated counterclockwise centrally about the rotation axis Og, whereas the gear 354 is rotated clockwise centrally about the rotation axis Og. Consequently, the pair of arms 346, 346 and the grippers 348, 353 are rotated symmetrically in the YZ plane about the standard axis, thereby enabling opening and closing operations to be performed.

Figure 22:
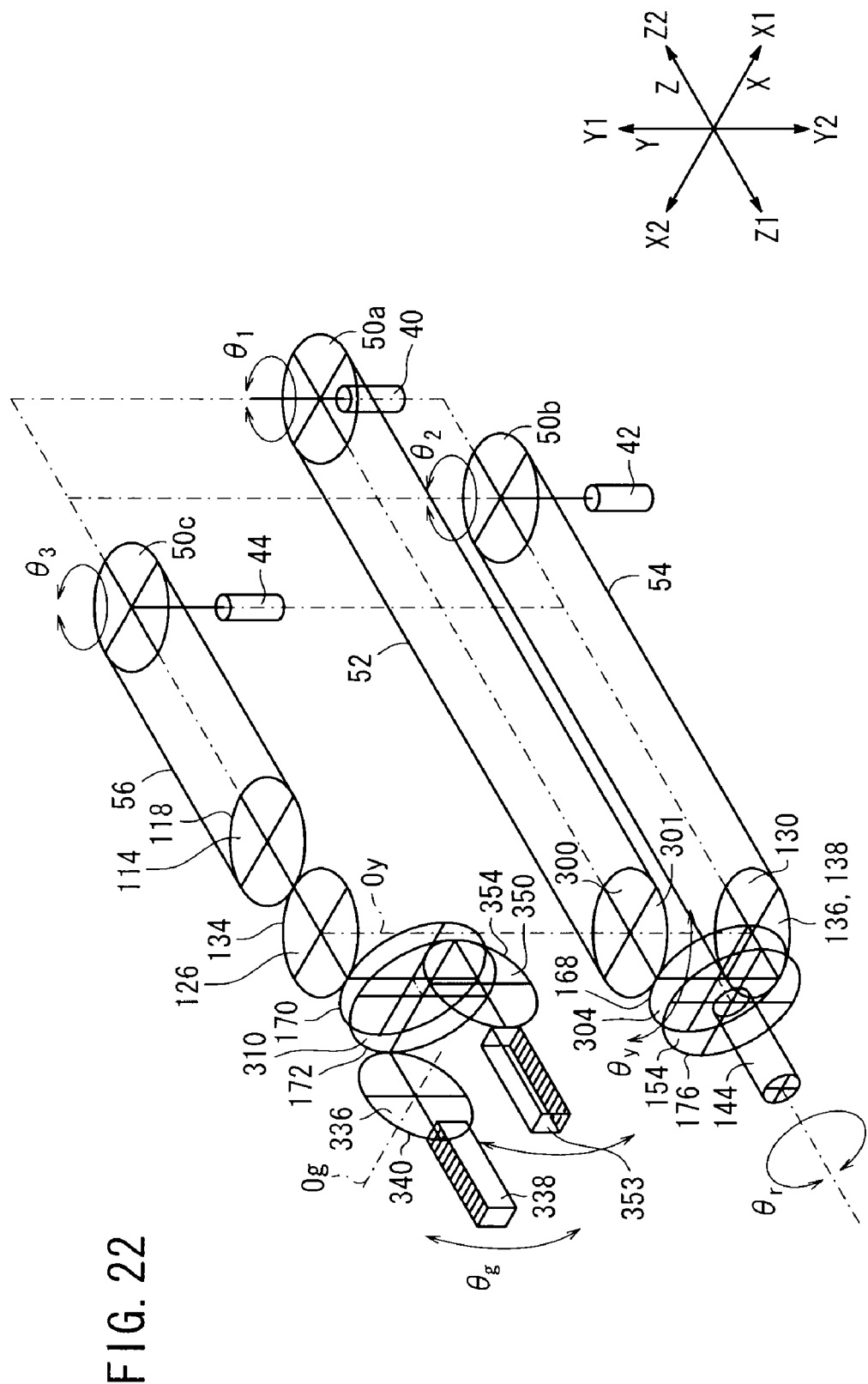
FIG. 22 is a basic schematic view of a drive system of the manipulator according to the second embodiment.

Next, operations of the manipulator 10b constructed in the foregoing manner shall be described below with reference to FIG. 22.

First, the manipulator 10b is actuated in a yawing direction by operating the first instruction lever 34 (see FIG. 1) with the finger. Specifically, when a surgeon handling the manipulator 10b operates the first instruction lever 34 with the finger, the motors 40 and 42 (see FIG. 1) are energized to rotate the drive pulleys 50a and 50b to circulatively drive the wires 52 and 54 in the same direction and at the same speed, thus rotating the main axis member 128 and the drive base 304 centrally about the first rotational axis Oy, and thereby swinging the end effector in yawing directions.

The manipulator 10b is actuated in a rolling direction by operating the second instruction lever 36 (see FIG. 1) with the finger. Specifically, when a surgeon handling the manipulator 10b operates the second instruction lever 36 with the finger, the motors 40 and 42 (see FIG. 1) are energized to rotate the drive pulleys 50a and 50b to circulatively drive the wires 52 and 54 in opposite directions, or at different speeds in the same direction, thus rotating the main axis member 128 and the drive base 304 centrally about the standard axis C, and thereby moving the end effector in rolling directions.

In this manner, for effecting movements in the yawing direction as well as movements in the rolling direction, the gear 301 and the gear 138 are driven by the differential mechanism. By utilizing the differential mechanism, the motors 40 and 42 cooperate to drive the gears 301 and 138, whereby the applied torque burden is shared in half by each of the motors 40 and 42.

The end effector 104 is selectively opened and closed by pulling the trigger lever 32 (see FIG. 1) with the finger. Specifically, by pulling the trigger lever 32 with the finger, the motor 44 (see FIG. 1) is energized to rotate the drive pulley 50c, thereby circulatively moving the wire 56 and rotating the gear body 114, the rotation of which is transmitted to the gear 134 and the face gears 170, 172. The face gear 172 rotates the gear 340 and the first end effector body 320 in a given direction, while the gear 354 and the second end effector body 322 are rotated in the opposite direction. Consequently, opening and closing operations of the end effector 104 can be carried out.

Next, an explanation shall be made concerning how the mechanism of the manipulator 10b utilizes the mathematical expressions. When the foregoing equation (2) is implemented and developed with respect to the manipulator 10b, the relational expressions corresponding to the foregoing equations (3-1), (3-2) and (3-3) are expressed by the following equations (7-1), (7-2) and (7-3). To simplify matters, in the following equations, each of the reduction ratios is set at 1.

$$\begin{bmatrix} \theta_1 \\ \theta_2 \\ \theta_3 \end{bmatrix} = \begin{bmatrix} 1 & 1 & 0 \\ 1 & -1 & 0 \\ -1 & -1 & 1 \end{bmatrix} \begin{bmatrix} \theta_y \\ \theta_r \\ \theta_{g'} \end{bmatrix} \quad (7\text{-}1)$$

$$\begin{bmatrix} \theta_y \\ \theta_r \\ \theta_{g'} \end{bmatrix} = \begin{bmatrix} 0.5 & 0.5 & 0 \\ 0.5 & -0.5 & 0 \\ 1 & 0 & 1 \end{bmatrix} \begin{bmatrix} \theta_1 \\ \theta_2 \\ \theta_3 \end{bmatrix} \quad (7\text{-}2)$$

$$\begin{bmatrix} \tau_1 \\ \tau_2 \\ \tau_3 \end{bmatrix} = \begin{bmatrix} 0.5 & 0.5 & 1 \\ 0.5 & -0.5 & 0 \\ 0 & 0 & 1 \end{bmatrix} \begin{bmatrix} \tau_y \\ \tau_r \\ \tau_{g'} \end{bmatrix} \quad (7\text{-}3)$$

Each of the axial torques upon gripping movement of the end effector 104 is investigated. The gripper axis torque required for gripping movement is provisionally set to $\tau_{g'}=1$. At this time, the ratios of the driving torques for each of the motors 40, 42, 44 are determined by substituting the values $\tau_y=0$, $\tau_r=0$ and $\tau_{g'}=1$ into equation (7-3).

$$\tau_1=1, \tau_2=0, \tau_3=1 \quad (8)$$

Herein, the different values of $\tau_1$ and $\tau_2$ corresponding to the first axis and the second axis of the same structure is based on the fact that the arrangement of the drive system for the third axis is not arranged symmetrically with respect to the central axis, but rather, is arranged on only one side thereof.

These are the values that are shown by the third column of equation (7-3). In this manner, when a gripping movement occurs, and when a torque of $\tau_{g'}=1$ is generated by the third axis motor 44, for the first axis motor 40, a torque which is one times the torque of the third axis motor 44 is required as an interference torque. Although the first axis receives a reactive force of the third axis, because the reactive force is in balance and cancels out on the yaw axis, it can be understood that a structure results in which the torques of the third axis and the first axis are not cumulatively added, and thus the second axis does not receive any torque therefrom.

Elongation of the wires of each of the drive systems is as shown below, assuming the rigidity of each of the wires to be equivalent.

$$\theta_1=1, \theta_2=0, \theta_3=1 \quad (9)$$

Tentatively, in the event that elongation of the wires corresponding as shown above to each of the axes occurs, the amount of posture variation caused by elongation of the wires can be obtained by substituting the wire elongation amounts into equation (7-2), as follows.

$$\theta_y=0.5, \theta_r=0.5, \theta_{g'}=2 \quad (10)$$

With the configuration of the manipulator 10a, since the values of $\theta_y$ and $\theta_r$ are such that $\theta_y=2$ and $\theta_r=3$ (refer to equation (6)), when compared with the manipulator 10a in which no control is performed for compensating posture, the manipulator 10b enables the posture variation to be reduced by ¼ on the yaw axis and by ⅙ on the roll axis.

Moreover, although the value of $\theta_{g'}$ is such that $\theta_{g'}=2$, the gripper axis to which this value corresponds only carries out a closing movement, and therefore, variations in posture are not generated thereby.

In this manner, in accordance with the manipulator 10b of the second embodiment, by means of the compound mechanism 102, although the torque $\tau_{g'}$ for driving the end effector 104 under operation of the motor 44 causes an interference torque to be generated on the motor 40, the torque $\tau_{g'}$ and the interference torque act on the motor 42 in such directions that they balance out with respect to the motor 42.

Next, a manipulator 10c according to a third embodiment shall be described.

As shown in FIGS. 23 to 26, at the working unit 12c of the manipulator 10c, the gear body 126, the gear body 300, and the main axis member 360 (second drive rotor) 360 are axially supported in succession with respect to the shaft 112, from the Y1 direction toward the Y2 direction.

The main axis member 360 is an element corresponding to the aforementioned main axis member 128, and in the same manner as the manipulator 10a discussed above, the main axis member 360 is driven through the wire 52 by the motor 40. In the main axis member 360, the axial portion thereof projects somewhat in the Y2 direction (see FIG. 26), and the wire 52 is wound around the axial portion.

The gear body 300 is driven by the motor 42 through the wire 54. Further, the gear body 130 of the manipulator 10b is not provided. In other structural aspects, the manipulator 10c is the same as the aforementioned manipulator 10b.

Figure 27:
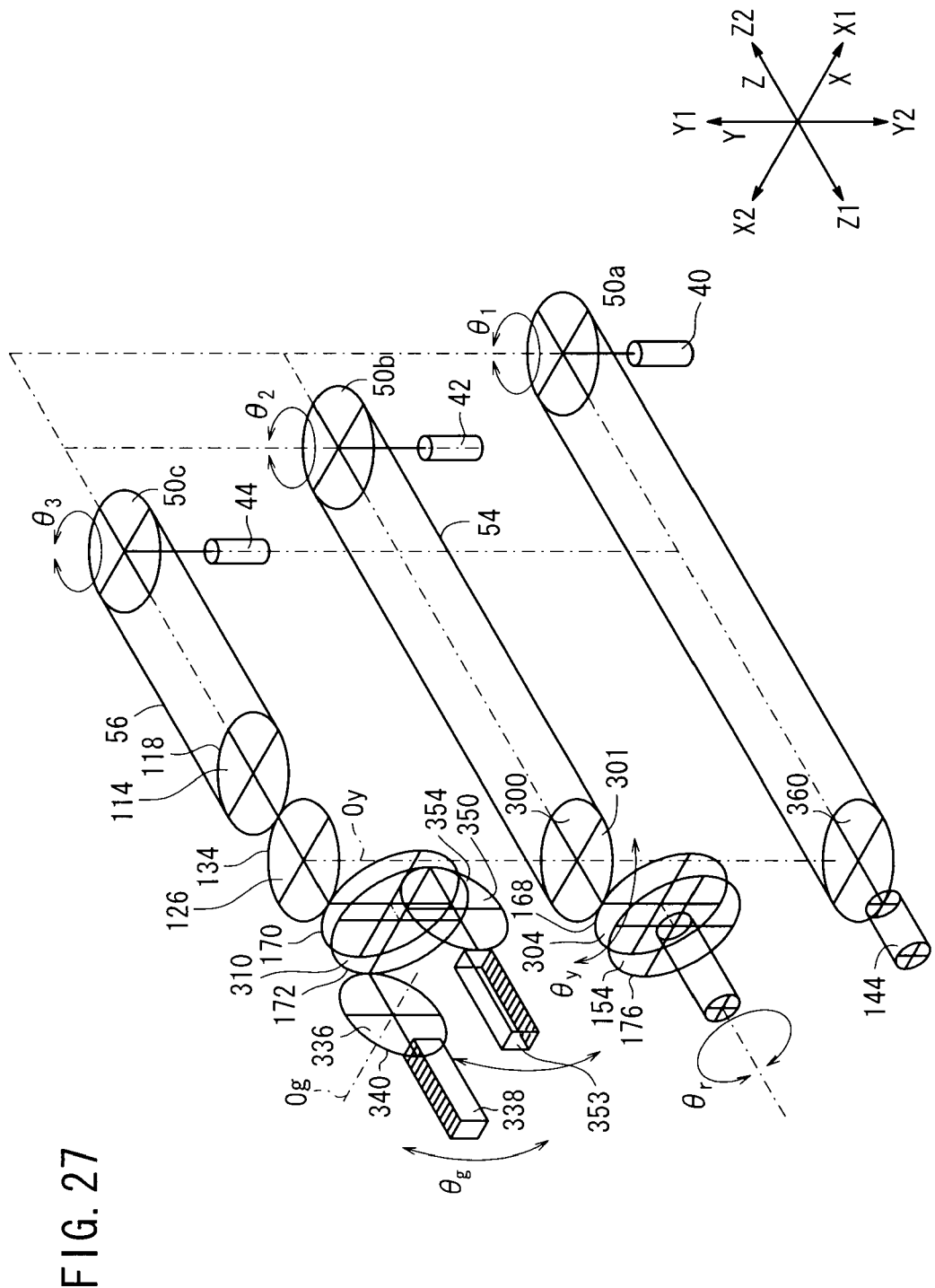
FIG. 27 is a basic schematic view of a drive system for the manipulator according to the third embodiment.

The basic structure of the drive system for the manipulator 10c is shown in FIG. 27. As can be easily understood by comparing the configuration shown in FIG. 27 with the basic structure of the drive system for the manipulator 10a (see FIG. 7), in the manipulator 10c, movements in the yaw axis direction are driven by the same mechanism as that of the manipulator 10a, under operation of the motor 40. As for gripper axis movements, although the structure of the gripper itself differs from the manipulator 10a, gripper axis movements are driven basically by the same mechanism under operation of the motor 44.

Concerning movement in the roll axis direction, because the gear 301 meshes with the top portion in the Y1 direction of the face gear 168, compared to the manipulator 10a in which the gear 138 meshes with the top portion in the Y2 direction of the face gear 168, in the case that the same motion is made, the direction of rotation of the motor 42 is reversed.

Next, an explanation shall be made concerning how the mechanism of the manipulator 10c utilizes the mathematical expressions. When the foregoing equation (2) is implemented and developed with respect to the manipulator 10c, the relational expressions corresponding to the foregoing equations (3-1), (3-2) and (3-3) are expressed by the following equations (11-1), (11-2) and (11-3). To simplify matters, in the following equations, each of the reduction ratios is set at 1.

$$\begin{bmatrix} \theta_1 \\ \theta_2 \\ \theta_3 \end{bmatrix} = \begin{bmatrix} 1 & 0 & 0 \\ 1 & 1 & 0 \\ -1 & -1 & 1 \end{bmatrix} \begin{bmatrix} \theta_y \\ \theta_r \\ \theta_{g'} \end{bmatrix} \quad (11\text{-}1)$$

$$\begin{bmatrix} \theta_y \\ \theta_r \\ \theta_{g'} \end{bmatrix} = \begin{bmatrix} 1 & 0 & 0 \\ -1 & 1 & 0 \\ 0 & 1 & 1 \end{bmatrix} \begin{bmatrix} \theta_1 \\ \theta_2 \\ \theta_3 \end{bmatrix} \quad (11\text{-}2)$$

$$\begin{bmatrix} \tau_1 \\ \tau_2 \\ \tau_3 \end{bmatrix} = \begin{bmatrix} 1 & -1 & 0 \\ 0 & 1 & 1 \\ 0 & 0 & 1 \end{bmatrix} \begin{bmatrix} \tau_y \\ \tau_r \\ \tau_{g'} \end{bmatrix} \quad (11\text{-}3)$$

Each of the axial torques upon gripping movement of the end effector 104 is investigated. The gripper axis torque required for gripping movement is provisionally set to $\tau_{g'}=1$. At this time, the ratios of the driving torques for each of the drive axes are determined by substituting the values $\tau_y=0$, $\tau_r=0$ and $\tau_g=1$ into equation (11-3).

$$\tau_1=0, \tau_2=1, \tau_3=1 \quad (12)$$

These are the values that are shown by the third column of equation (11-3). In this manner, when a gripping movement occurs, and when a torque of $\tau_g=1$ is generated by the third axis motor 44, for the second axis motor 42, a torque which is one times the torque of the third axis motor 44 is required as an interference torque. Although the second axis receives a reactive force of the third axis, because the reactive force is in balance on the yaw axis, it can be understood that a structure results in which the torques of the third axis and the second axis are not cumulatively added, and thus the first axis does not receive any torque therefrom.

That is, by positioning the gear 301 for driving the roll axis and the gear 134 for driving the gripper, on the same side (i.e., the Y1 side in FIG. 27) with respect to the main axis member 360, the drive torque for the yaw axis portion can be kept in balance.

Elongation of the wires of each of the drive systems is as shown below, assuming the rigidity of each of the wires to be equivalent.

$$\theta_1=0, \theta_2=1, \theta_3=1 \quad (13)$$

With this structure, in which the reactive forces (interference torques) are not cumulatively added, as shown below, the yaw axis is in a state of balance with minimal reactive forces (interference torques).

Tentatively, in the event that elongation of the wires corresponding as shown above to each of the axes occurs, the amount of posture variation caused by elongation of the wires can be obtained by substituting the wire elongation amounts into equation (11-2), as follows.

$$\theta_y=0, \theta_r=1, \theta_{g'}=2 \quad (14)$$

With the configuration of the manipulator 10a, since the value of $\theta_y$ and $\theta_r$ are such that $\theta_y=2$ and $\theta_r=3$ (refer to equation (6)), when compared with the manipulator 10a in which no control is performed for compensating posture, the manipulator 10c enables the posture variation to be reduced by ⅓ on the roll axis. Concerning the yaw axis, a configuration is enabled in which no posture variation whatsoever is exhibited on the yaw axis.

Further, with the manipulator 10c, the gear 134, the gear 301, and the main axis member 360 are all arranged in succession with respect to the shaft 112. Stated otherwise, the gear 134 that serves to drive the gripper axis at the tip end is arranged in an outermost position, which is rational from a structural standpoint.

Further, according to the above equation (11-1), for causing motion of $\theta_r$ from 0 to 1 (0→1), it is necessary for $\theta_2$ to be moved from 0 to 1 (0→1) and for $\theta_3$ to be moved from 0 to −1 (0→−1). That is, in the case that the roll axis is driven in a plus direction, the second axis is driven in a plus direction, while the third axis is moved in a minus direction. By transforming equation (11-3), the following equation (11-4) is obtained.

$$\begin{bmatrix} \tau_y \\ \tau_r \\ \tau_{g'} \end{bmatrix} = \begin{bmatrix} 1 & 1 & -1 \\ 0 & 1 & -1 \\ 0 & 0 & 1 \end{bmatrix} \begin{bmatrix} \tau_1 \\ \tau_2 \\ \tau_3 \end{bmatrix} \quad (11\text{-}4)$$

In the case that the roll axis is positively (+) driven, and when the frictional torque of the drive system by the compound mechanism with respect to $\theta_2$ and $\theta_3$ is large, a frictional torque of $+\tau_2'$ is added to $\tau_2$ and a frictional torque of $-\tau_3'$ is added to $\tau_3$. In accordance with equation (11-4), this results in an interference torque on the yaw axis, such that $\tau_y$ becomes $\tau_y=\tau_2'+\tau_3'$, and the interference torque is added in the same direction, thereby causing swinging motion of the yaw axis. In the case that such unnecessary swinging motion cannot be ignored, correction of a target position in the plus direction may be carried out on the first axis. Conversely, in the case that the roll axis is driven in the minus direction, correction of a target position in the minus direction may be carried out on the first axis.

The correcting direction of the target position of the first axis depends on the movement direction of the roll axis. Accordingly, based on a change (from a positive direction to a negative direction, or from a negative direction to a positive direction) in the movement direction of the roll axis, the torque detector section detects the timing thereof, whereby the direction of correction may be switched or changed over.

In the event that viscous frictional torque is dominant, the first axis correction amount may be made proportional to the roll axis movement. In other words, based on the velocity of the posture axis, a control may be performed to shift the movement position of the corresponding posture axis actuator. On the other hand, in the event that Coulomb frictional torque is dominant, a constant value, considering only the rotation direction of the roll axis, is acceptable. It is a matter of course that control may be effected taking both viscous frictional torque and Coulomb frictional torque under consideration.

In the case that Coulomb frictional torque is dominant and that only the rotation direction of the roll axis is considered, the switching timing may be at a timing at which velocity is generated.

More specifically, in the event that the velocity exceeds zero and rotation occurs in a negative direction from a condition of positive rotation, timing is effected for switching control at the time that negative rotation occurs. In the event that the velocity exceeds zero and rotation occurs in a positive direction from a condition of negative rotation, timing is effected for switching control at the time that positive rotation occurs.

In the event that rotation occurs again in the positive direction after the velocity reaches zero from a condition of positive rotation, as well as in the case that rotation occurs again in the negative direction after the velocity reaches zero from a condition of negative rotation, it is unnecessary to perform control switching. This is because, normally, at the time zero velocity is reached, a condition is retained prior to the Coulomb friction becoming zero.

It is a matter of course that the compensation control of the posture variation carried out by the manipulator 10a may also be used in combination with both the manipulators 10a and 10b.

Comparisons between the given torque ratio, the wire elongation ratio, and the posture variation amount ratio, of each of the axes during a gripping operation of the gripper, in the manipulator 10a (in the case that compensation control is not carried out), the manipulator 10b, and the manipulator 10c, are summarized in FIG. 28. The differential mechanism of the manipulator 10b, and the same side pinion arrangement mechanism of the manipulator 10c exhibit effects for all of the given torques, the wire elongation ratios, and the posture variation amounts of each of the axes during gripping operations of the gripper, compared with values of the manipulator 10a (in the case that compensation control is not carried out). The numerical values shown inside parenthesis are comparative values with the numerical values of the manipulator 10a.

The manipulators 10a to 10c and the working units 12a to 12c are capable of being applied to a remote operation mechanism for performing techniques through an electronic communications means or the like, from a location separated from the YR grasping forceps, the needle driver and the patient. Of course, the invention may suitably be applied to other manipulators apart from those used for medical treatments, for example, as a manipulator used for repairing narrow regions of energy-related devices and the like.

The working mechanism and manipulator according to the present invention are not limited to the aforementioned embodiments. It should be understood that various other configurations may be adopted without deviating from the scope of the invention as set forth in the appended claims.

What is claimed is:

1. A manipulator comprising:
    a working unit including an end effector axis and at least one posture axis by which an orientation of said end effector axis is changed;
    a mechanical unit disposed on said working unit for operating said end effector axis and said posture axis;
    an end effector axis actuator for driving said end effector axis, and at least one posture axis actuator for driving said posture axis;
    a controller for controlling movement positions of said end effector axis actuator and said posture axis actuator, thereby operating said end effector axis and said posture axis; and
    a torque generation detector for detecting a timing at which torque is generated on at least one of said end effector axis and said posture axis,
    wherein, when said torque generation detector detects said timing, said controller controls the movement position of said posture axis actuator so as to be shifted by a predetermined amount in a same direction as a direction at which an interference torque is generated by said mechanical unit, and
    wherein said torque generation detector detects said timing based on said end effector axis reaching an end of a movement range.

2. The manipulator according to claim 1, wherein said posture axis actuator and said posture axis are connected together via a flexible member.

3. The manipulator according to claim 1, wherein the predetermined amount by which the movement position of said posture axis actuator is shifted is variably set based on the torque detected by said torque generation detector.

4. The manipulator according to claim 1, wherein said torque generation detector detects said timing based on a current value that drives said end effector axis actuator.

5. The manipulator according to claim 1, wherein said torque generation detector detects said timing based on a difference between a command position of said end effector axis actuator and an actual position thereof.

6. The manipulator according to claim 1, wherein said at least one posture axis actuator includes a plurality of posture axis actuators, and said controller controls and shifts a movement position of a corresponding one of said posture axis actuators, based on a velocity of said posture axis.

7. The manipulator according to claim 1, wherein:
    said at least one posture axis includes a plurality of posture axes and said at least one posture axis actuator includes a plurality of posture axis actuators, wherein a generated interference torque value on each of said posture axes is different; and
    said controller controls and shifts a movement position of a corresponding one of said posture axis actuators by a difference amount on each of said posture axes, based on a calculated value of the generated interference torque.

8. The manipulator according to claim 1, wherein said mechanical unit comprises:
    a face gear that faces a proximal end side; and
    a protective plate that covers at least a part of said face gear.

9. The manipulator according to claim 1, wherein said mechanical unit comprises:
    a gear that rotates centrally about a perpendicular axis, which is perpendicular to an extending axial direction of said working unit; and
    a protective plate that covers said gear when said protective plate is projected in a direction of said perpendicular axis.

10. A manipulator comprising:
    a working unit including an end effector axis and at least one posture axis by which an orientation of said end effector axis is changed;
    a mechanical unit disposed on said working unit for operating said end effector axis and said posture axis;
    an end effector axis actuator for driving said end effector axis, and at least one posture axis actuator for driving said posture axis;
    a controller for controlling movement positions of said end effector axis actuator and said posture axis actuator, thereby operating said end effector axis and said posture axis; and
    a torque generation detector for detecting a timing at which torque is generated on at least one of said end effector axis and said posture axis,
    wherein, when said torque generation detector detects said timing, said controller controls the movement position of said posture axis actuator so as to be shifted by a predetermined amount in a same direction as a direction at which an interference torque is generated by said mechanical unit, and
    wherein said torque generation detector detects said timing based on a change in a movement direction of said posture axis.

11. The manipulator according to claim 10, wherein said posture axis actuator and said posture axis are connected together via a flexible member.

12. The manipulator according to claim 10, wherein the predetermined amount by which the movement position of said posture axis actuator is shifted is variably set based on the torque detected by said torque generation detector.

13. The manipulator according to claim 10, wherein said torque generation detector detects said timing based on a current value that drive said end effector axis actuator.

14. The manipulator according to claim 10, wherein said torque generation detector detects said timing based on a difference between a command position of said end effector axis actuator and an actual position thereof.

15. The manipulator according to claim 10, wherein said at least one posture axis actuator includes a plurality of posture axis actuators, and said controller controls and shills a movement position of a corresponding one of said posture axis actuators, based on a velocity of said posture axis.

16. The manipulator according to claim 10, wherein:
    said at least one posture axis includes a plurality of posture axis and said at least one posture axis actuator includes a plurality of posture axis actuators,
    wherein a generated interference torque value on each of said posture axis is different; and
    said controller controls and shifts a movement position of a corresponding one of said posture axis actuators by a difference amount on each of said posture axis, based on a calculated value of the generated interference torque.

17. A method for controlling a manipulator, said manipulator comprising:
 a working unit including an end effector axis and at least one posture axis by which an orientation of said end effector axis is changed;
 a mechanical unit disposed on said working unit for operating said end effector axis and said posture axis;
 an end effector axis actuator for driving said end effector axis, and at least one posture axis actuator for driving said posture axis; and
 a controller for controlling movement positions of said end effector axis actuator and said posture axis actuator, thereby operating said end effector axis and said posture axis,
 said method comprising the steps of:
 providing a torque generation detector for detecting a timing at which torque is generated on at least one of said end effector axis and said posture axis; and
 when said torque generation detector detects said timing based on said end effector axis reaching an end of a movement range, controlling, by said controller, the movement position of said posture axis actuator so as to be shifted by a predetermined amount in a same direction as a direction at which an interference torque is generated by said mechanical unit.

18. A method for controlling a manipulator, said manipulator comprising:
 a working unit including an end effector axis and at least one posture axis by which an orientation of said end effector axis is changed;
 a mechanical unit disposed on said working unit for operating said end effector axis and said posture axis;
 an end effector axis actuator for driving said end effector axis, and at least one posture axis actuator for driving said posture axis; and
 a controller for controlling movement positions of said end effector axis actuator and said posture axis actuator, thereby operating said end effector axis and said posture axis,
 said method comprising the steps of:
 providing a torque generation detector for detecting a timing at which torque is generated on at least one of said end effector axis and said posture axis; and
 when said torque generation detector detects said timing based on a change in a movement direction of said posture axis, controlling, by said controller, the movement position of said posture axis actuator so as to be shifted by a predetermined amount in a same direction as a direction at which an interference torque is generated by said mechanical unit.

* * * * *